United States Patent
Machhammer et al.

(10) Patent No.: US 7,321,058 B2
(45) Date of Patent: Jan. 22, 2008

(54) METHOD FOR PRODUCING ACROLEIN AND/OR ACRYLIC ACID

(75) Inventors: Otto Machhammer, Mannheim (DE); Christoph Adami, Weinheim (DE); Claus Hechler, Ludwigshafen (DE); Peter Zehner, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/297,579

(22) PCT Filed: Jun. 13, 2001

(86) PCT No.: PCT/EP01/06708

§ 371 (c)(1), (2), (4) Date: Dec. 12, 2002

(87) PCT Pub. No.: WO01/96271

PCT Pub. Date: Dec. 20, 2001

(65) Prior Publication Data

US 2003/0187299 A1   Oct. 2, 2003

(30) Foreign Application Priority Data

Jun. 14, 2000 (DE) ................... 10028582

(51) Int. Cl.
 *C07C 51/16* (2006.01)
 *C07C 51/42* (2006.01)

(52) U.S. Cl. ...................... 562/545; 562/549

(58) Field of Classification Search ............... 562/549, 562/311, 312, 545, 600

See application file for complete search history.

(56) References Cited

U.S. PATENT DOCUMENTS

| 3,161,670 | A |   | 12/1964 | Adams et al. ............... 558/320 |
| 3,798,283 | A | * | 3/1974 | Bitar et al. .................. 585/656 |
| 3,862,256 | A |   | 1/1975 | Isailingold et al. ......... 585/626 |
| 3,887,631 | A |   | 6/1975 | Yaffe .......................... 585/624 |
| 3,932,500 | A | * | 1/1976 | Duembgen et al. ......... 562/600 |
| 4,220,091 | A |   | 9/1980 | Israels et al. ............... 102/487 |
| 4,255,284 | A |   | 3/1981 | Hardman .................... 502/211 |
| 4,341,664 | A |   | 7/1982 | Antos ......................... 502/329 |

(Continued)

FOREIGN PATENT DOCUMENTS

CA  1 217 502  2/1987

(Continued)

OTHER PUBLICATIONS

Aldrich , p. 1560, 1998-1999. p. 2.*

(Continued)

*Primary Examiner*—Taylor Victor Oh
(74) *Attorney, Agent, or Firm*—Oblon, Spivak, McClelland, Maier & Neustadt, P.C.

(57) ABSTRACT

Acrolein and/or acrylic acid are prepared from propane and/or propene by a process comprising the following steps: (a) separation of propane and/or propene from a propane- and/or propene-containing gas mixture by absorption in an absorbent, (b) separation of the propane and/or propene from the absorbent to give a gas B and (c) use of the gas B obtained in stage (b) for an oxidation of propane and/or propene to acrolein and/or acrylic acid, no heterogeneously catalyzed dehydrogenation of propane without supply of oxygen being carried out between steps (b) and (c).

38 Claims, 4 Drawing Sheets

U.S. PATENT DOCUMENTS

Figure 1:
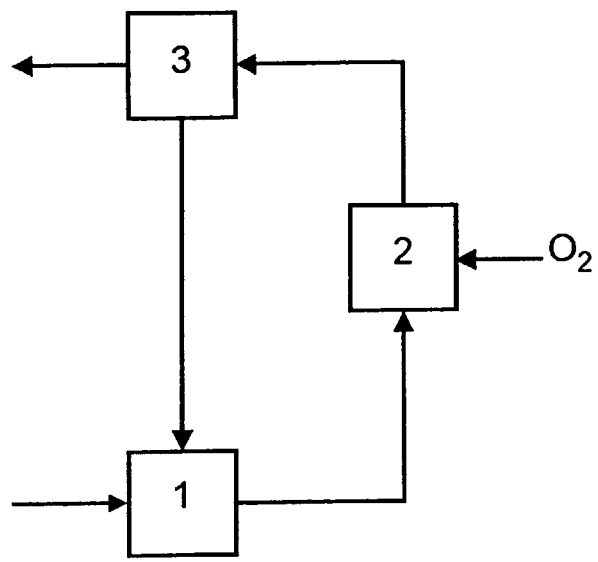

| | | | |
|---|---|---|---|
| 4,532,365 A * | 7/1985 | Khoobiar | 568/479 |
| 4,788,371 A | 11/1988 | Imai et al. | 585/443 |
| 4,886,928 A | 12/1989 | Imai et al. | 585/315 |
| 4,902,849 A | 2/1990 | McKay et al. | 585/660 |
| 4,996,387 A | 2/1991 | Gerhold et al. | 585/654 |
| 5,073,662 A | 12/1991 | Olbrich | 585/660 |
| 5,086,032 A | 2/1992 | Mazzocchia et al. | 502/315 |
| 5,183,936 A | 2/1993 | Etzkorn et al. | 562/532 |
| 5,198,578 A | 3/1993 | Etzkorn et al. | 562/532 |
| 5,389,342 A | 2/1995 | Savage et al. | 422/109 |
| 5,430,209 A | 7/1995 | Agaskar et al. | 585/659 |
| 5,430,220 A | 7/1995 | Khare et al. | 585/660 |
| 5,527,979 A | 6/1996 | Agaskar et al. | 585/654 |
| 5,530,171 A | 6/1996 | Agaskar et al. | 585/659 |
| 5,563,314 A | 10/1996 | Agaskar et al. | 585/654 |
| 5,877,369 A | 3/1999 | Wu et al. | 585/419 |
| 5,994,580 A * | 11/1999 | Takahashi et al. | 562/549 |
| 6,388,129 B1 * | 5/2002 | Machhammer et al. | 562/545 |

FOREIGN PATENT DOCUMENTS

| | | |
|---|---|---|
| CN | 1073893 | 7/1993 |
| CN | 1 105 352 | 7/1995 |
| DE | 28 30 765 | 1/1980 |
| DE | 29 096 71 | 10/1980 |
| DE | 33 13 573 | 10/1983 |
| DE | 41 32 263 | 4/1993 |
| DE | 43 08 087 | 9/1994 |
| DE | 44 31 949 | 3/1995 |
| DE | 44 31 957 | 3/1995 |
| DE | 43 35 172 | 4/1995 |
| DE | 44 36 243 | 4/1996 |
| DE | 195 08 532 | 9/1996 |
| DE | 195 30 454 | 2/1997 |
| DE | 196 22 331 | 12/1997 |
| DE | 198 35 247 | 2/1999 |
| DE | 197 53 817 | 6/1999 |
| DE | 199 29 487 | 6/1999 |
| DE | 198 37 517 | 2/2000 |
| DE | 198 37 518 | 2/2000 |
| DE | 198 37 519 | 2/2000 |
| DE | 198 37 520 | 2/2000 |
| DE | 100 51 419 | 6/2000 |
| DE | 199 10 506 | 9/2000 |
| DE | 199 10 508 | 9/2000 |
| DE | 199 24 532 | 11/2000 |
| DE | 199 24 533 | 11/2000 |
| DE | 199 37 105 | 2/2001 |
| DE | 199 37 107 | 2/2001 |
| DE | 199 37 196 | 3/2001 |
| DE | 199 52 964 | 5/2001 |
| DE | 100 46 672 | 12/2001 |
| EP | 0 017 000 | 10/1980 |
| EP | 0 117 146 | 8/1984 |
| EP | 0 253 409 | 1/1988 |
| EP | 0 293 224 | 11/1988 |
| EP | 0 529 853 | 3/1993 |
| EP | 0 575 879 | 12/1993 |
| EP | 0 608 838 | 8/1994 |
| EP | 0 700 714 | 3/1996 |
| EP | 0 700 893 | 3/1996 |
| EP | 0 731 077 | 9/1996 |
| EP | 0 767 164 | 4/1997 |
| EP | 0 895 809 | 2/1999 |
| EP | 0 705 136 | 3/1999 |
| EP | 0 911 313 | 4/1999 |
| EP | 0 962 253 | 12/1999 |
| EP | 0 979 813 | 2/2000 |
| EP | 0 982 289 | 3/2000 |
| EP | 0 990 636 | 4/2000 |
| FR | 2 754 817 | 4/1998 |
| GB | 1 378 178 | 12/1974 |
| JP | 6-227819 | 8/1994 |
| JP | 7-53448 | 2/1995 |
| JP | 7-232071 | 9/1995 |
| JP | 8-57319 | 3/1996 |
| JP | 10-28862 | 2/1998 |
| JP | 10-36311 | 2/1998 |
| JP | 10-57813 | 3/1998 |
| JP | 10-310539 | 11/1998 |
| JP | 10-330343 | 12/1998 |
| JP | 11-42434 | 2/1999 |
| JP | 11-43314 | 2/1999 |
| JP | 11-57479 | 3/1999 |
| JP | 11-169716 | 6/1999 |
| JP | 11-263745 | 9/1999 |
| JP | 11-285637 | 10/1999 |
| JP | 11-343261 | 12/1999 |
| JP | 11-343262 | 12/1999 |
| JP | 2000/26123 | 1/2000 |
| JP | 2000-37623 | 2/2000 |
| JP | 2000-51693 | 2/2000 |
| WO | 97/36849 | 10/1997 |
| WO | 99/03825 | 1/1999 |
| WO | 99/29420 | 6/1999 |
| WO | 99/46039 | 9/1999 |
| WO | WO 00/10960 * | 3/2000 |
| WO | 00/29105 | 5/2000 |
| WO | 00/29106 | 5/2000 |
| WO | 00/39065 | 7/2000 |

OTHER PUBLICATIONS

Robert K. Grasselli Catalysis Today 49, pp. 141-153 1999.
Hiromu Watanabe et al. Applied Catalysis A: General 194 to 195, pp. 479-485 2000.
W. Ueda et al. Kinetics and Catalysis, vol. 40, No. 3, pp. 401-404 1999.
W. Ueda et al. Chem. Commun., pp. 517-518 1999.
Kenji Nomiya et al. POLYHEDRON, vol. 6, No. 2, pp. 213-218 1987.
Young-Chul Kim et al. Applied Catalysis, vol. 70, No. 2, pp. 175-187 1991.
Y.-C Kim et al. Catalysis Today 13, pp. 673-678 1992.
W. Zhang et al. Catalysis Letters 23, pp. 103-106 1994.
Z. Huang Shiydu Huagong 21, p. 592 1992.
David L. Stern et al. J. of Catalysis 167, pp. 560-569 1997.
David L. Stern et al. J. of Catalysis 167, pp. 550-559 1997.
Young Seek Yoon et al. Topics in Catalysis 3, pp. 265-275 1996.
C. Mazzocchia et al. Catalysis Letters 10, pp. 181-192 1991.
Luis E. Cadus et al. Ind. Eng. Chem. Res., vol. 35, pp. 14-18 1996.
R. Burch et al. Applied Catalysis A: General 100, pp. 111-130 1993.
Xingtao Gao et al. J. of Catalysis 148, pp. 56-67, 1993.
V. Cortes et al., eds. New Developments in Selective Oxidation II, Elsevier Science B.V., pp. 305-313 1994.
R.K. Grasselli et al., eds. 3rd World Congress on Oxidation Catalysis, Elsevier Science B.V., pp. 375 et sqq. 1997.
W. Zhang Gaodeng Xuexiao Huaxue Xuebao, vol. 14, p. 566 1993.

* cited by examiner

METHOD FOR PRODUCING ACROLEIN AND/OR ACRYLIC ACID

The present invention relates to a process for the preparation of acrolein and/or acrylic acid from propane and/or propene.

Acrolein and acrylic acid are key chemicals. Thus, acrylic acid is used, inter alia, as a monomer for the preparation of polymers which, for example as a dispersion in an aqueous medium, are used as binders. Depending on the intended use of the polymer, an esterification of the acrylic acid may also take place before the polymerization. Acrolein is an important intermediate, for example for the preparation of glutaraldehyde, methionine, folic acid and acrylic acid.

Known processes for the preparation of acrolein and/or acrylic acid start from propane and/or propene. DE-A 33 13 573 and EP-A-0 117 146 disclose a process for converting propane into acrolein and/or acrylic acid. A two-stage or three-stage process in which the propane is dehydrogenated to propene in a first stage and the propene is oxidized to acrolein in a second stage is described. An important feature here is that no separation of the propane from secondary components formed in the dehydrogenation, for example molecular hydrogen, is carried out between the two stages. The oxidation is carried out under conditions under which no marked oxidation of the hydrogen takes place. In a third stage, the acrolein can then be oxidized to acrylic acid. It is also possible to separate off unconverted propane and propene from the second or third stage by absorption and, after liberation from the absorbent, to recycle them to the first stage (dehydrogenation stage).

Japanese Patent Application JP-A 10-36311 discloses a process for the preparation of α,β-unsaturated carboxylic acids, such as acrylic acid, by gas-phase catalytic oxidation of propane in the presence of a composite metal oxide catalyst, the ratio of propane to oxygen and, if required, diluent gas being kept in a defined range for achieving high yields in the starting mixture and furthermore the conversion being kept at a specific value. Unconverted propane can be separated off after the oxidation by a selective separator which comprises pressure swing adsorption units and then recycled to the gas-phase catalytic oxidation.

GB 1378-178 discloses a process in which unconverted hydrocarbon from an oxidation process is absorbed in an absorbent and the absorbent is stripped with a stripping medium. In this, the hydrocarbon to be recovered is added to the stripping medium in such a quantity that the mixture is outside the flammable limits.

It is an object of the present invention to provide a process for the gas-phase catalytic preparation of acrolein and/or acrylic acid from propane and/or propene, which is economical and in which the catalyst used can be employed for a very long time without regeneration.

We have found that this object is achieved, according to the invention, by absorption of propane and/or propene from a propane- and/or propene-containing gas mixture into an absorbent, separation of the propane and/or propene from the absorbent and subsequent use of the propane and/or propene for an oxidation to acrolein and/or acrylic acid.

The present invention therefore relates to a process for the preparation of acrolein and/or acrylic acid from propane and/or propene, the process comprising the following steps:

(a) separation of propane and/or propene from propane- and/or propene-containing gas mixture A by absorption into an absorbent, (b) separation of the propane and/or propene from the absorbent to give a propane- and/or propene-containing gas B and (c) use of the gas B obtained in step (b) for an oxidation of propane and/or propene to acrolein and/or acrylic acid, no heterogeneously catalyzed dehydrogenation of propane without a supply of oxygen being carried out between step (b) and step (c). Preferred embodiments of the invention are evident from the following description and the figures.

Since the propane and/or propane are subjected to absorption before the oxidation, as a rule residues of absorbent are present in the gas B. Surprisingly, it has now been found that nevertheless no problems occur during the oxidation. Thus, no substantial decrease in the activity of the oxidation catalyst was observed, and the oxidation catalyst could be used over a long operating period without regeneration. Furthermore, no problems due to any expected concomitant oxidation of residues of absorbent in the oxidation stage were observed. Where residues of the absorbent present problems, which is generally not the case when hydrocarbons having a high boiling point, in particular paraffins, are used as the absorbent, said absorbent can be removed, for example by quenching with water or by adsorption.

In the process according to DE-A 33 13 573, propane and propene recovered by absorption or separated off are recycled to the heterogeneously catalyzed dehydrogenation of propane. In the heterogeneously catalyzed propane dehydrogenation, the catalyst may be deactivated, for example by coking. Such dehydrogenation catalysts are therefore frequently regenerated. The absorbent fed in together with the gas stream therefore presents no problems since it can be incinerated together with the coke. On the other hand, the catalysts used in the oxidation to acrolein and/or acrylic acid are usually not regenerated so often because the additional regeneration cost which arises by virtue of the fact that the feed gas contains absorbent is greater than in the case of dehydrogenation. The novel process has the advantage that the oxidation catalyst can be used over a long period without regeneration.

The novel process differs from the process according to DE-A 33 13 573 in that the propane and/or propene separated off by absorption is/are fed to an oxidation stage. In contrast to the situation in the process according to DE-A 33 13 573, there is, according to the invention, no heterogeneously catalyzed dehydrogenation of propane without supply of oxygen between the separation of propane and/or propene from the absorbent and the oxidation to acrolein and/or acrylic acid.

In the present invention, the gas B may also be a gas mixture.

In step (a), gas mixtures A comprising any desired amounts of propane and/or propene can be used. Preferably, the gas mixture A contains propane and propene in a molar ratio of from 0:100 to 100:0, in particular from 10:90 to 90:10, frequently from 80:20 to 40:60.

Preferably, the gas mixture A contains at least one further component which differs from propane and/or propene and is not subject to any particular restrictions. As a rule, the further components depend on the origin of the gas mixture. In particular, they comprise at least one component selected from nitrogen, hydrogen, oxides of carbon, such as carbon monoxide or carbon dioxide, further secondary components originating from a propane dehydrogenation, secondary components originating from a gas-phase oxidation of propene to acrolein and/or acrylic acid or secondary components originating from an oxidation of propane to acrolein and/or acrylic acid. Frequently, at least hydrogen, nitrogen, an oxide of carbon or a mixture of these is present as a further component.

Suitable absorbents in step (a) are in principle all absorbents which are capable of absorbing propane and/or propene. The absorbent is preferably an organic solvent which is preferably hydrophobic and/or high-boiling. Advantageously, this solvent has a boiling point (at an atmospheric pressure of 1 atm) of at least 120° C., preferably of at least 180° C., especially from 200 to 350° C., in particular from 250 to 300° C., more preferably from 260 to 290° C. Expediently, the flashpoint (at an atmospheric pressure of 1 atm) is above 110° C. In general, suitable absorbents are relatively nonpolar organic solvents, for example aliphatic hydrocarbons which preferably contain no externally acting polar group, but also aromatic hydrocarbons. In general, it is desirable for the absorbent to have a very high boiling point in combination with very high solubility for propane and/or propene. Examples of absorbents are aliphatic hydrocarbons, for example $C_8$-$C_{20}$-alkanes or $C_8$-$C_{20}$-alkenes, or aromatic hydrocarbons, for example middle oil fractions from paraffin distillation or ethers having bulky groups on the oxygen atom, or mixtures thereof, it being possible to add to them a polar solvent, for example, the 1,2-dimethyl phthalate disclosed in DE-A 43 08 087. Esters of benzoic acid and phthalic acid with straight-chain alkanols of 1 to 8 carbon atoms, such as n-butyl benzoate, methyl benzoate, ethyl benzoate, dimethyl phthalate and diethyl phthalate, and thermal oils, such as biphenyl, diphenyl ether and mixtures of biphenyl and diphenyl ether or their chlorine derivatives and triarylalkenes, for example 4-methyl-4'-benzyldiphenylmethane and its isomers 2-methyl-2'-benzyldiphenylmethane, 2-methyl-4'-benzyldiphenylmethane and 4-methyl-2' -benzyldiphenylmethane, and mixtures of such isomers are furthermore suitable. A suitable absorbent is a solvent mixture comprising biphenyl and diphenyl ether, preferably in the azeotropic composition, in particular comprising about 25% by weight of biphenyl and about 75% by weight of diphenyl ether, for example the commercially available diphyl. Frequently, this solvent mixture contains an added solvent, such as dimethyl phthalate, in an amount of from 0.1 to 25% by weight, based on the total solvent mixture. Other particularly suitable absorbents are octanes, nonanes, decanes, undecanes, dodecanes, tridecanes, tetradecanes, pentadecanes, hexadecanes, heptadecanes and octadecanes, tetradecane having proven particularly suitable. It is advantageous if the absorbent used on the one hand has the abovementioned boiling point but on the other hand simultaneously has not too high a molecular weight. Advantageously, the molecular weight of the absorbent is $\leq 300$ g/mol. The liquid paraffins of 8 to 10 carbon atoms which are described in DE-A 33 13 573 are also suitable. Examples of suitable commercial products are products sold by Haltermann, such as Halpasols i, e.g. Halpasol 250/340 i and Halpasol 250/275 i, and printing ink oils with the names PKWF and Printosol.

The absorption procedure is not subject to any particular restrictions. All processes and conditions familiar to a person skilled in the art may be used. Preferably, the gas mixture is brought into contact with the absorbent at from 1 to 50, preferably from 2 to 20, more preferably from 5 to 10, bar and from 0 to 100° C., in particular from 30 to 50° C. The absorption can be carried out both in columns and in quench apparatuses. The cocurrent or the countercurrent procedure may be employed. Suitable absorption columns are, for example, tray columns (having bubble trays and/or sieve trays), columns having stacked packings (for example sheet metal packings having a specific surface area of from 100 to 500 $m^2/m^3$, for example Mellapak® 250 Y) and columns having dumped packings (for example filled with Raschig packings). However, trickle and spray towers, graphite block absorbers, surface absorbers, such as thick-film and thin-film absorbers, and plate scrubbers, cross-spray scrubbers and rotary scrubbers may also be used. It may also be advantageous to allow the absorption to take place in a bubble column with or without internals.

The separation of the propane and/or propene from the absorbent can be effected by stripping, flashing and/or distillation.

The separation of the propane and/or propene from the absorbent in step (b) is preferably effected by stripping or desorption with a gas which is inert with respect to the novel step (c) and/or with molecular oxygen (for example air). Here, the stripping can be carried out in the usual manner via a pressure and/or temperature change, preferably at from 0.1 to 10, in particular from 1 to 5, more preferably from 1 to 2, bar and from 0 to 200° C., in particular from 20 to 100° C., more preferably from 30 to 50° C. Another gas suitable for the stripping is, for example steam, but oxygen/nitrogen mixtures are particularly preferred, for example air. With the use of air or oxygen/nitrogen mixtures in which the oxygen content is more than 10% by volume, it may be expedient to add, before or during the stripping process, a gas which reduces the explosion range. Particularly suitable for this purpose are gases having a specific heat capacity of >29 J/mol·K at 20° C., for example methane, ethane, propane, butane, pentane, hexane, benzene, methanol, ethanol, ammonia, carbon dioxide or water. Bubble columns with or without internals are also particularly suitable for the stripping.

The separation of the propane and/or propene from the absorbent can also be effected by means of distillation, it being possible to use the columns familiar to a person skilled in the art and containing stacked packings, dumped packings or corresponding internals.

Preferred conditions during the distillation are a pressure of from 0.01 to 5, in particular from 0.1 to 3, more preferably from 1 to 2, bar and a temperature (at the bottom) of from 50 to 300° C., in particular from 150 to 250° C.

Where the gas mixture A contains water, the absorption is advantageously combined with a condensation of the water (i.e. water quench). It is also advantageous to follow the desorption step with a water quench in order to minimize the losses of absorbent.

Frequently, step (c) is carried out directly after step (b), i.e. without process steps in between or intermediate stages. However, after step (b) and before step (c) absorbent can be separated, for example by a water quench.

The oxidation of propene and/or propane to acrolein and/or acrylic acid, which is carried out in step (c), can be effected according to all processes which are known to a person skilled in the art and are not subject to any restrictions. In step (c), a one-stage or two-stage oxidation of propene to acrolein and/or acrylic acid or an oxidation of propane to acrolein and/or acrylic acid or both, i.e. simultaneous oxidation of propane and propene to acrolein and/or acrylic acid, can be carried out. The oxidation is expediently carried out as a selective, heterogeneously catalyzed gas-phase oxidation with molecular oxygen to give an acrolein- and/or acrylic acid-containing product gas mixture. If required, the propane and/or propene fed to the oxidation is brought beforehand, by indirect heat exchange, to the reaction temperature required for the oxidation reaction.

In a preferred embodiment, step (c) of the novel process is carried out as an oxidation of propene to acrolein and/or acrylic acid.

In principle, the heterogeneously catalyzed gas-phase oxidation of propene to acrylic acid with molecular oxygen takes place in two steps in succession along the reaction coordinate, the first of which leads to acrolein and the second from acrolein to acrylic acid. This reaction sequence in two successive steps makes it possible, in a manner known per se, to carry out the step (c) of the novel process in two oxidation zones arranged one behind the other, it being possible for the oxidic catalyst to be used to be adapted in an optimum manner in each of the two oxidation zones. Thus, as a rule a catalyst based on multimetal oxides containing the combination of elements Mo—Bi—Fe is preferred for the first oxidation zone (propene→acrolein), while catalysts based on multimetal oxides containing the combination of elements Mo—B are usually preferred for the second oxidation zone (acrolein→acrylic acid). Corresponding multimetal oxide catalysts for the two oxidation zones have been widely described and are well known to a person skilled in the art. For example, EP-A-0 253 409 refers to corresponding U.S. patents on page 5. Advantageous catalysts for the two oxidation zones are also disclosed in DE-A 44 31 957 and DE-A 44 31 949. This applies in particular to those of the formula I in the two abovementioned publications. As a rule, the product mixture from the first oxidation zone is transferred without intermediate treatment into the second oxidation zone.

The simplest form for realizing the two oxidation zones is therefore a tube-bundle reactor, within which the catalyst load changes correspondingly along the individual catalyst tubes with the end of the first reaction step. Such oxidations are described, for example, in EP-A-0 911 313, EP-A-0 979 813, EP-A-0 990 636 and DE-A 28 30 765). If required, the catalyst load in the catalyst tubes is interrupted by an inert bed.

Preferably, however, the two oxidation zones are realized in the form of two tube-bundle systems connected in series. These may be present in a reactor, the transition from one tube bundle to another tube bundle being formed by a bed of inert material not housed in the catalyst tube and expediently accessible. While the heat-transfer medium generally flows around the catalyst tubes, said heat-transfer medium does not reach an inert bed installed as described above. The two catalyst tube bundles are therefore advantageously housed in reactors spatially separated from one another. As a rule, an intermediate condenser is present between the two tube-bundle reactors in order to reduce any subsequent acrolein combustion in the product gas mixture which leaves the first oxidation zone. Instead of tube-bundle reactors, plate-type heat exchanger reactors with salt cooling and/or evaporative cooling, as described, for example, in DE-A 199 29 487 and DE-A 199 52 964, can also be used.

The reaction temperature in the first oxidation zone is as a rule from 300 to 450° C., preferably from 320 to 390° C. The reaction temperature in the second oxidation zone is as a rule from 200 to 300° C., frequently from 220 to 290° C. The reaction pressure in both oxidation zones is expediently from 0.5 to 5, advantageously from 1 to 3, atm. The gas loading (l(S.T.P.)/l·h) of the oxidation catalysts with reaction gas is frequently from 1500 to 2500 $h^{-1}$ or up to 4000 $h^{-1}$ in both oxidation zones. The propene loading (l(S.T.P.)/l·h) is frequently from 50 to 300 $h^{-1}$, in particular from 100 to 200 $h^{-1}$.

In principle, the two oxidation zones can be designed as described, for example, in DE-A 198 37 517, DE-A 199 10 506, DE-A 199 10 508 and DE-A 198 37 519. Usually, the external heating in the two oxidation zones, if desired in multizone reactor systems, is adapted in a manner known per se to the specific composition of the reaction gas mixture and to the catalyst load.

According to the invention, it is advantageous if, in the novel process, propene-accompanying propane acts as an advantageous inert diluent gas in a heterogeneously catalyzed propene oxidation.

The total molecular oxygen required for the oxidation can be added beforehand to the gas B in its total amount. However, oxygen may also be added to said gas after the first oxidation zone.

Preferably, a molar propene:molecular oxygen ratio of from 1:1 to 1:3, frequently from 1:1.5 to 1:2, is established in the first oxidation zone. In the second oxidation zone, a molar acrolein: molecular oxygen ratio of from 1:0.5 to 1:2 is preferably established.

In both oxidation zones, an excess of molecular oxygen generally has an advantageous effect on the kinetics of the gas-phase oxidation. Since the heterogeneously catalyzed gas-phase oxidation of the propene to acrylic acid is subject to kinetic control, the propene can in principle therefore be initially taken in a molar excess relative to the molecular oxygen, for example also in the first oxidation zone. In this case, the excess propene factually plays the role of a diluent gas.

In principle, the heterogeneously catalyzed gas-phase oxidation of propene to acrylic acid can however also be realized in a single oxidation zone. In this case, the two reaction steps take place in an oxidation reactor which is loaded with a catalyst which is capable of catalyzing the reaction of both reaction steps. Here, the catalyst load can also change continuously or abruptly along the reaction coordinate within the oxidation zone. In an embodiment of step (c) in the form of two oxidation zones connected in series, it is also possible partly or completely to separate, from the product gas mixture leaving the first oxidation zone, oxides of carbon and steam contained in said mixture and formed as byproduct in the first oxidation zone, if required before further passage into the second oxidation zone. Preferably, a procedure which does not require such a separation is chosen.

Suitable sources for the molecular oxygen required in the oxidation step (c) are both pure molecular oxygen and molecular oxygen diluted with inert gas, such as carbon dioxide, carbon monoxide, noble gases, nitrogen and/or saturated hydrocarbons.

In an expedient manner, air is used as an oxygen source at least for covering part of the requirement of molecular oxygen. The gas B fed to the oxidation step (c) of the novel process advantageously comprises substantially only propane and propene, and exclusively air is used as a source of molecular oxygen for the oxidation. If required, cooling of the gas B fed to step (c) can also be effected in a direct manner by metering in cold air.

If acrolein is the desired product, the second oxidation zone is expediently not used in step (c).

The oxidation of propene to acrolein and/or acrylic acid in step (c) can also be carried out as described in EP-A-0 117 146, U.S. Pat. No. 5,198,578 and U.S. Pat. No. 5,183,936 or analogously to DE-A 33 13 573, CA-A-1 217 502, U.S. Pat. No. 3,161,670, U.S. Pat. No. 4,532,365 and WO 97/36849. Suitable processes are also described in EP-A-0 293 224, EP-A-0 253 409, DE-A 44 31 957, DE 195 08 532 or DE-A 41 32 263, particularly preferred processes being those which operate with diluent gases in the oxidation.

The oxidation of acrolein to acrylic acid can be carried out as described in WO 00/39065, by means of a fluidized-bed reactor.

The oxidation of propene to acrolein and/or acrylic acid can also be carried out using the plate-type heat exchanger reactors described in DE-A 199 52 964.

In a further preferred embodiment, step (c) of the novel process is carried out as an oxidation of propane to acrolein and/or acrylic acid. In this oxidation, propane is converted over a suitable catalyst, in one or more stages, to acrolein and/or acrylic acid. All processes known to a person skilled in the art are suitable for this purpose. A suitable process is described, for example, in JP-A-10 36 311.

Catalysts suitable for the heterogeneously catalyzed gas-phase oxidation of propane to acrolein and/or acrylic acid are multimetal oxide materials of the formula (I)

$$MoV_bM^1_cM^2_dO_n \quad (I)$$

where

M$^1$ is Te and/or Sb,

M$^2$ is at least one of the elements from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is from 0.01 to 1, c is from >0 to 1, preferably from 0.01 to 1, d is from >0 to 1, preferably from 0.01 to 1, and n is a number which is determined by the valency and frequency of the elements other than oxygen in (I).

Multimetal oxide materials which have stoichiometry corresponding to the formula (I) are known, cf for example EP-A-0 608 838, EP-A-0 529 853, JP-A 7-232 071, JP-A 10-57813, JP-A 2000-37623, JP-A 10-36311, WO 00/29105, Proceedings ISO 99, Rimini (Italy), Sep. 10-11, 1999, G. Centi and S. Perathoner Ed., SCI Pub. 1999, EP-A-0 767 164, Catalysis Today 49 (1999), 141-153, EP-A-0 962 253, Applied Catalysis A: General 194 to 195 (2000), 479 to 485, JP-A 11/169716, EP-A-0 895 809, DE-A 198 35 247, JP-A 857319, JP-A 10-28862, JP-A 11-43314, JP-A 11-57479, WO 00/29106, JP-A 10-330343, JP-A 11-285637, JP-A 10-310539, JP-A 11-42434, JP-A 11-343261, JP-A 11-343262, WO 99/03825, JP-A 7-53448, JP-A 2000-51693 and JP-A 11-263745.

The multimetal oxides (I), (II) and (III) described below are particularly suitable.

In the multimetal oxide materials (I) of the formula (I), M$^1$ is Te and/or Sb; M$^2$ is at least one of the elements from the group consisting of Nb, Ta, W, Ti, Al, Zr, Cr, Mn, Fe, Ru, Co, Rh, Ni, Pd, Pt, Bi, B and Ce; b is from 0.01 to 1; c is from 0.01 to 1; d is from 0.01 to 1; and n is a number which is determined by the valency and frequency of the elements other than oxygen in (I).

The preparation of a multimetal oxide material (I) is preferably carried out by a procedure in which a mixture of sources of the elemental constituents of the multimetal oxide material (I) is subjected to hydrothermal treatment and the freshly forming solid is separated off and is converted into an active oxide by thermal treatment. In the multimetal oxide material (I), M$^1$ is preferably Te, M$^2$ is preferably Nb, b is preferably 0.1-0.6, c is preferably 0.05-0.4 and d is preferably 0.01-0.6. The thermal treatment is preferably carried out at from 350 to 700° C., the thermal treatment initially being effected in particular at from 150 to 400° C. under an oxygen-containing atmosphere and then at from 350 to 700° C. under an inert gas atmosphere. Suitable stoichiometries for the multimetal oxide materials (I) are those which are disclosed in EP-A-0 608 838, WO 00/29106, JP-A 11/169716 and EP-A-0 962 253.

The hydrothermal preparation of multimetal oxide active material precursors is familiar to a person skilled in the art (cf. for example Applied Catalysis A: 194 to 195 (2000), 479-485, Kinetics and Catalysis, 40, No. 3 (1999), 401 to 404, Chem. Commun. (1999), 517 to 518, JP-A 6/227819 and JP-A 2000/26123).

What is understood here in particular is the thermal treatment of a preferably intimate mixture of sources of the elemental constituents of the desired multimetal oxide material (I) in a high-pressure vessel (autoclave) in the presence of steam at superatmospheric pressure, usually at from >100 to 600° C. The pressure range is typically up to 500, preferably up to 250, atm. Temperatures above 600° C. and steam pressures above 500 atm may also be used, but this is not very expedient in terms of application technology. The hydrothermal treatment is particularly advantageously carried out under conditions under which steam and liquid water coexist. This is possible in a temperature range from >100 to 374.15° C. (critical temperature of water) using the corresponding pressures. The amounts of water are expediently such that the liquid phase is capable of holding the total amount of the starting compounds in suspension and/or solution.

However, a procedure in which the intimate mixture of the starting compounds completely absorbs the amount of liquid water present in equilibrium with the steam is also possible.

Advantageously, the hydrothermal treatment is carried out at from >100 to 300° C., preferably from 150 to 250° C. (for example from 160 to 180° C.). Based on the sum of water and sources of the elemental constituents of the desired multimetal oxide material (I), the amount of the latter in the autoclave is as a rule at least 1% by weight. Usually, the abovementioned amount is not above 90% by weight. Amounts of from 3 to 60 or from 5 to 30, frequently from 5 to 15, % by weight are typical.

During the hydrothermal treatment, stirring may or may not be effected. Particularly suitable starting compounds (sources) for the hydrothermal preparation variant are all those which are capable of forming oxides and/or hydroxides on heating with water under superatmospheric pressure. Oxides and/or hydroxides of the elemental constituents may also be concomitantly or exclusively used as starting compounds for the hydrothermal preparation. As a rule, the sources are used in finely divided form.

Suitable sources for the elemental constituents are all those which are capable of forming oxides and/or hydroxides on heating (if necessary in air). Oxides and/or hydroxides of the elemental constituents may be concomitantly or exclusively used as such starting compounds.

Suitable sources of the element Mo are, for example, molybdenum oxides, such as molybdenum trioxide, molybdates, such as ammonium heptamolybdate tetrahydrate and molybdenum halides, such as molybdenum chloride.

Suitable starting compounds to be used concomitantly with the element V are, for example, vanadyl acetylacetonate, vanadates, such as ammonium metavanadate, vanadium oxides, such as vanadium pentoxide (V$_2$O$_5$), vanadium halides, such as vanadium tetrachloride (VCl$_4$), and vanadium oxyhalides, such as VOCl$_3$. Expediently, vanadium starting compounds which are concomitantly used are those which contain the vanadium in oxidation state +4.

Suitable sources for the element tellurium are tellurium oxides, such as tellurium dioxide, metallic tellurium, tellurium halides, such as TeCl$_2$, and telluric acids, such as orthotelluric acid H$_6$TeO$_6$.

Advantageous antimony starting compounds are antimony halides, such as $SbCl_3$, antimony oxides, such as antimony trioxide ($Sb_2O_3$), antimonic acids, such as $HSb(OH)_6$, and antimony oxide salts, such as antimony oxide sulfate ($SbO_2)SO_4$.

Suitable niobium sources are, for example, niobium oxides, such as niobium pentoxide ($Nb_2O_5$), niobium oxyhalides, such as $NbOCl_3$, niobium halides, such as $NbCl_5$, and complex compounds of niobium and organic carboxylic acids and/or dicarboxylic acids, for example oxalates and alcoholates. The Nb-containing solutions used in EP-A-0 895 809 are also suitable as a niobium source.

Regarding all other possible elements $M^2$, particularly suitable starting compounds are their halides, nitrates, formates, oxalates, acetates, carbonates and/or hydroxides. Suitable starting compounds are often also their oxo compounds, for example tungstates, or the acids derived from these. Frequently, ammonium salts are also used as starting compounds.

Other suitable starting compounds are polyanions of the Anderson type, as have been described, for example, in Polyhedron 6, No. 2 (1987), 213-218, and have been used, for example, in Applied Catalysis A: General 194-195 (2000), 479-485, for the preparation of suitable multimetal oxides (I) or are disclosed in the secondary literature cited therein. A further suitable literature source for polyanions of the Anderson type is Kinetics and Catalysis, 40 (1999), 401 to 404.

Further polyanions suitable as starting compounds are, for example, those of the Dawson or Keggin type. Preferably used starting compounds are those which are converted into their oxides at elevated temperatures either in the presence or in the absence of oxygen, possibly with liberation of gaseous compounds.

The hydrothermal treatment itself takes, as a rule, a period of from a few hours to a few days. A period of 48 hours is typical. It is expedient in terms of application technology if the autoclave to be used for the hydrothermal treatment is coated on the inside with Teflon. Before the hydrothermal treatment, the autoclave, if required including the aqueous mixture contained, may be evacuated. It can then be filled with inert gas ($N_2$; noble gas) before the temperature is increased. Both measures may also be omitted. The aqueous mixture may additionally be flushed with inert gas for blanketing prior to the hydrothermal treatment. It is also expedient in terms of application technology if the above-mentioned inert gases are used for establishing superatmospheric pressure in the autoclave before the hydrothermal treatment.

The required treatment of the solid freshly formed in the course of the hydrothermal treatment and separated off after the end of the hydrothermal treatment (after the end of the hydrothermal treatment, the autoclave can be either quenched to room temperature or brought to room temperature slowly, i.e. over a relatively long period (for example by leaving it to stand)) is expediently carried out at from 350 to 700° C., frequently from 400 to 650° C. or from 400 to 600° C. It can be effected under an oxidizing, reducing or inert atmosphere. A suitable oxidizing atmosphere is, for example, air, air enriched with molecular oxygen or air depleted in oxygen. Preferably, the thermal treatment is carried out under an inert atmosphere, i.e. for example under molecular nitrogen and/or noble gas. Of course, the thermal treatment can also be effected under reduced pressure.

If the thermal treatment is carried out under a gaseous atmosphere, this may be either stationary or flowing.

In general, the thermal treatment may take up to 24 hours or more.

The thermal treatment is preferably carried out initially under an oxidizing (oxygen-containing) atmosphere (for example under air) at from 150 to 400° C. or from 250 to 350° C. The thermal treatment is then expediently continued under inert gas at from 350 to 700° C. or from 400 to 650° C. or from 400 to 600° C. The thermal treatment of the hydrothermally produced catalyst precursor can also be effected in such a way that the catalyst precursor material is first pelleted, then thermally treated and subsequently converted into chips.

It is expedient in terms of application technology if the solid obtained in the hydrothermal treatment is converted into chips for the subsequent thermal treatment.

If the starting compounds used for the preparation of the multimetal oxide materials (I) are the same as those used for a conventional preparation of multimetal oxides (I) and the thermal treatment of the conventionally produced intimate dry blend is carried out in the same way as the thermal treatment of the hydrothermally obtained solid, the multimetal oxide materials (I) generally have a higher selectivity of the acrylic acid formation and a higher activity with respect to the heterogeneously catalyzed gas-phase oxidation of propane to acrylic acid under the same conditions.

The multimetal oxide materials (I) can be used as such (for example after comminution to a powder or to chips) or can be converted into moldings before being used. The catalyst bed may be either a fixed bed, a moving bed or a fluidized bed.

The X-ray diffraction pattern of the multimetal oxide materials (I) corresponds as a rule essentially to those in EP-A-0 529 853, DE-A 198 35 247 and EP-A-0 608 838.

The multimetal oxide materials (I) can also be used in a form diluted with finely divided, for example colloidal, materials, such as silica, titanium dioxide, alumina, zirconium oxide or niobium oxide.

The mass dilution ratio may be up to 9 (diluent): 1 (active material). This means that possible mass dilution ratios are also 6 (diluent): 1 (active material) and 3 (diluent): 1 (active material). The diluent can be incorporated before and/or after the calcination. As a rule, the diluent is incorporated before the hydrothermal treatment. If the incorporation is effected before the calcination, the diluent must be chosen so that it is substantially retained as such during the calcination. The same applies to the hydrothermal treatment in the case of incorporation before said treatment is carried out. As a rule, this is true, for example, in the case of oxides calcined at correspondingly high temperatures.

Other catalysts suitable for the propane oxidation are multimetal oxide materials (II) which have the abovementioned formula (I) and whose X-ray diffraction pattern has reflections h, i and k whose peaks are at the diffraction angles (2θ) 22.2±0.4° (h), 27.3±0.4° (i) and 28.2±0.4° (k), where the reflection h is the one with the highest intensity within the X-ray diffraction pattern and has a half-width of not more than 0.5°, the intensity Pi of the reflection i and the intensity $P_k$ of the reflection k fulfill the relationship $0.65 \leq R \leq 0.85$, in which R is the intensity ratio defined by the formula $R=P_i/(P_i+P_k)$, and the half-width of the reflection i and of the reflection k is $\leq 1°$ in each case.

Preferably, 0.67 <R<0.75 and very particularly preferably R=0.70 to 0.75 or R 0.72.

The use of multimetal oxide materials (II) where $M^1$ is Te is preferred. Furthermore, those multimetal oxide materials (II) in which $M^2$ is Nb, Ta, W and/or Ti are advantageous. Preferably, $M^2$ is Nb.

The stoichiometric coefficient b of the multimetal oxide materials (II) is advantageously from 0.1 to 0.6. In a corresponding manner, the preferred range for the stoichiometric coefficient c is from 0.01 to 1 or from 0.05 to 0.4 and advantageous values for d are from 0.01 to 1 or from 0.1 to 0.6. Particularly advantageous multimetal oxide materials (II) are those in which the stoichiometric coefficients b, c and d are simultaneously in the abovementioned preferred ranges. Further suitable stoichiometries for the multimetal oxide materials (II) are those which are disclosed in the publications of the prior art cited above, in particular those disclosed in JP-A 7-53448.

A specific process for the preparation of multimetal oxide materials (II) is disclosed, for example, in JP-A 11-43314, in which the relevant multimetal oxide materials (II) are recommended as catalysts for the heterogeneously catalyzed oxydehydrogenation of ethane to ethene.

Thereafter, a multimetal oxide material of the formula (I) which is a mixture of the i-phase and other phases (for example k-phase) is first produced in a manner known per se and disclosed in the cited prior art publications. In this mixture, for example, the proportion of i-phase can be increased by selectively removing the other phases, for example the k-phase, under the microscope or washing the multimetal oxide material with suitable liquids. Suitable such liquids are, for example, aqueous solutions of organic acids (for example oxalic acid, formic acid, acetic acid, citric acid and tartaric acid), inorganic acids (for example nitric acid), alcohols and aqueous hydrogen peroxide solutions. Furthermore, JP-A 7-232071 discloses a process for the preparation of multimetal oxide materials (II).

Multimetal oxide materials (II) are obtainable by the preparation method according to DE-A 198 35 247. According to this, a very intimate, preferably finely divided, dry blend is produced from suitable sources of their elemental constituents and said dry blend is subjected to a thermal treatment at from 350 to 700° C. or from 400 to 650° C. or from 400 to 600° C. The thermal treatment can be carried out under either an oxidizing, reducing or inert atmosphere. A suitable oxidizing atmosphere is, for example, air, air enriched with molecular oxygen or air depleted in oxygen. Preferably, the thermal treatment is carried out under an inert atmosphere, i.e. for example under molecular nitrogen and/or noble gas.

Usually, the thermal treatment is effected at atmospheric pressure (1 atm). Of course, the thermal treatment can also be effected under reduced or superatmospheric pressure.

If the thermal treatment is carried out under a gaseous atmosphere, this may be either stationary or flowing. In general, the thermal treatment may take up to 24 hours or more.

The thermal treatment is initially preferably carried out under an oxidizing (oxygen-containing) atmosphere (for example under air) at from 150 to 400° C. or from 250 to 350° C. Thereafter, the thermal treatment is expediently continued under an inert gas at from 350 to 700° C. or from 400 to 650° C. or from 400 to 600° C. The thermal treatment can also be effected in such a way that the catalyst precursor material is first pelleted (if required after pulverization and, if required, with the addition of from 0.5 to 2% by weight of finely divided graphite) before its thermal treatment, then subjected to the thermal treatment and subsequently converted into chips.

The thorough mixing of the starting compounds in the preparation of the multimetal oxide materials (II) can be effected in dry or in wet form. If it is effected in dry form, the starting compounds are expediently used in the form of finely divided powders and, after mixing and any compaction, are subjected to the calcination (thermal treatment). However, the thorough mixing is preferably effected in wet form. Usually, the starting compounds are mixed with one another in the form of an aqueous solution and/or suspension. Thereafter, the aqueous material is dried and is calcined after the drying. Expediently, the aqueous material is an aqueous solution or an aqueous suspension. Preferably, the drying process is carried out immediately after the preparation of the aqueous mixture and by spray-drying (the outlet temperatures are as a rule from 100 to 150° C.; the spray-drying can be carried out by the cocurrent or countercurrent method), which requires a particularly intimate dry blend, especially when the aqueous material to be spray-dried is an aqueous solution or suspension.

Suitable sources or starting compounds for the multimetal oxide material (II) are the compounds described above in the case of the multimetal oxide material (I).

The multimetal oxide materials (II) can be converted into moldings as in the case of the multimetal oxide materials (I) and can be used in the same way as these. The shaping of the multimetal oxide materials (II) can be effected, for example, by application to a support, as described below under catalyst (III), or by extrusion and/or pelleting, both of finely divided multimetal oxide material (II) and of finely divided precursor material of a multimetal oxide material (II).

In the same way as the multimetal oxide materials (I), the multimetal oxide materials (II) can also be used in a form diluted with finely divided materials.

Suitable geometries are spheres, solid cylinders and hollow cylinders (rings). The longest dimension of the abovementioned geometries is as a rule from 1 to 10 mm. In the case of cylinders, their length is preferably from 2 to 10 mm and their external diameter preferably from 4 to 10 mm. In the case of rings, the wall thickness is moreover usually from 1 to 4 mm. Suitable annular unsupported catalysts may also have a length from 3 to 6 mm, an external diameter of from 4 to 8 mm and a wall thickness of from 1 to 2 mm. However, an annular unsupported catalyst having the dimensions of 7 mm×3 mm×4 mm or of 5 mm×3 mm×2 mm (external diameter x length x internal diameter) is also possible.

The definition of the intensity of a reflection in the X-ray diffraction pattern is based here on the definition stated in DE-A 198 35 247 and that in DE-A 100 51 419 and DE-A 100 46 672.

This means that if $A^1$ is the peak of a reflection 1 and $B^1$ is the next pronounced minimum (minima having the reflection shoulders are not taken into account) to the left of peak $A^1$ in the line of the X-ray diffraction pattern when viewed along the intensity axis perpendicular to the 2θ axis and $B^2$ is correspondingly the next pronounced minimum to the right of the peak $A^1$ and $C^1$ is a point at which a straight line drawn from the peak $A^1$ perpendicular to the 2θ axis intersects a straight line connecting the points $B^1$ and $B^2$, then the intensity of reflection 1 is the length of the straight line section $A^1C^1$ which extends from the peak $A^1$ to the point $C^1$. The expression minimum means a point at which the slope of a tangent to the curve in a base region of reflection 1 changes from a negative value to a positive value, or a point at which the slope tends to zero, the coordinates of the 2θ axis and of the intensity axis being used for specifying the slope.

Here, the half-width is correspondingly the length of the straight line section which is present between the two points of intersection $H^1$ and $H^2$ if a parallel to the 2θ axis is drawn in the center of the straight line section $A^1C^1$, $H^1$ and $H^2$ being in each case the first point of intersection of this parallel, to the left and right of $A^1$, with that line of the X-ray diffraction pattern which is defined as above.

Figure 6:
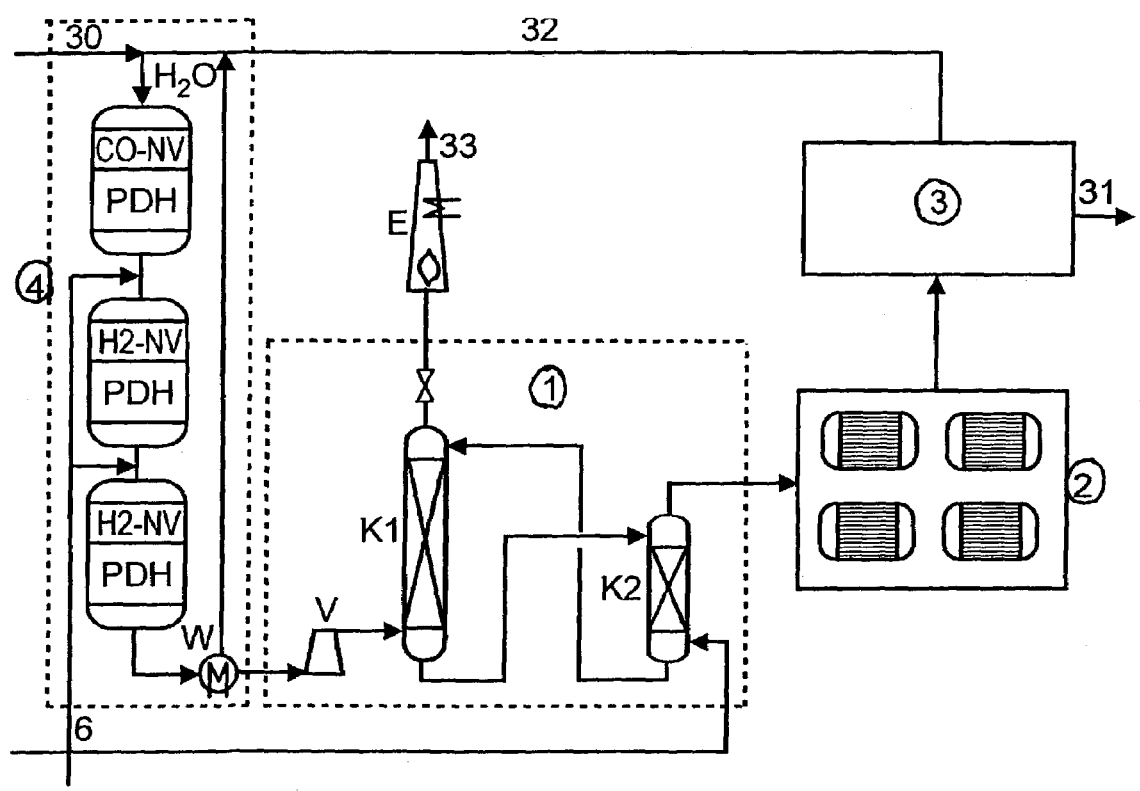

An exemplary procedure for the determination of half-width and intensity is also shown in FIG. 6 in DE-A 100 46 672.

In addition to the reflections h, i and k, the X-ray diffraction pattern of advantageous catalytically active multimetal oxide materials (II) contains, as a rule, further reflections whose peaks are at the following diffraction angles (2θ):

9.0±0.4° (l),
6.7±0.4° (o) and
7.9±0.4° (p).

It is advantageous if the X-ray diffraction pattern of the catalytically active oxide materials of the formula (I) additionally contains a reflection whose peak is at the following diffraction angle (2θ):

45.2±0.4° (q).

Frequently, the X-ray diffraction pattern of the multimetal oxide materials (II) also contains the reflections 29.2±0.4° (m) and 35.4±0.4° (n).

The multimetal oxide material (II) may be one whose X-ray diffraction pattern has no reflection with a peak position of 2θ=50.0±0.3°, i.e. one which contains no k-phase.

However, the multimetal oxide material (II) can also contain a k-phase, its X-ray diffraction pattern generally also containing further reflections whose peaks are at the following diffraction angles (2θ):

36.2±0.40 and
50.0±10.4°.

If the reflection h is assigned the intensity 100, it is advantageous if the reflections i, l, m, n, o, p and q have the following intensities on the same intensity scale:

i: from 5 to 95, frequently from 5 to 80, in some cases from 10 to 60;
l: from 1 to 30;
m: from 1 to 40;
n: from 1 to 40;
o: from 1 to 30;
p: from 1 to 30 and
q: from 5 to 60.

If the X-ray diffraction pattern contains additional reflections from those stated above, the half-width thereof is as a rule <1°.

All data based here on an X-ray diffraction pattern relate to an X-ray diffraction pattern produced using Cu—Kα radiation as the X-radiation (Siemens diffractometer Theta-Theta D-5000, tube voltage: 40 kV, tube current: 40 mA, aperture V20 (variable), collimator V20 (variable), secondary monochromator aperture (0.1 mm), detector aperture (0.6 mm), measuring interval (2θ): 0.02°, measuring time per step: 2.4 s, detector: scintillation counter).

The specific surface area of multimetal oxide materials (II) is often from 1 to 30 $m^2/g$ (BET surface area, nitrogen).

Another suitable catalyst for the propane oxidation is a catalyst (III) which consists of a support and a catalytically active oxide material of the abovementioned formula (I) which is applied to the surface of the support.

The use of oxide materials of the formula (I) where $M^1$ is Te is preferred. It is furthermore advantageous if $M^2$ is Nb, Ta, W and/or Ti. Preferably, $M^2$ is Nb.

The stoichiometric coefficient b of the oxide materials of the formula (I) in catalyst (III) is advantageously from 0.1 to 0.6. In a corresponding manner, the preferred range for the stoichiometric coefficient c is from 0.01 to 1 or from 0.05 to 0.4, and advantageous values for d are from 0.01 to 1 or from 0.1 to 0.6. Particularly advantageous oxide materials are those in which the stoichiometric coefficients b, c and d are simultaneously in the abovementioned preferred ranges.

Further suitable stoichiometries for the oxide materials of the formula (I) are those which are disclosed in the abovementioned publications, in particular those which are disclosed in EP-A-0 608 838, WO 00/29106, JP-A 11/169716 and EP-A-0 962 253.

The application of the above-described multimetal oxide material (II) as the oxide material of the formula (I) to a support is also particularly preferred for the preparation of the catalyst (III).

The supports are preferably chemically inert, i.e. they play substantially no part in the course of the catalytic gas-phase oxidation of propane to acrylic acid. Particularly suitable materials for the supports are alumina, silica, silicates, such as clay, kaolin, steatite, pumice, aluminum silicate and magnesium silicate, silicon carbide, zirconium dioxide and thorium dioxide.

The surface of the support may be either smooth or rough. Advantageously, the surface of the support is rough since increased surface roughness generally results in high adhesive strength of the applied active material coat.

Frequently, the surface roughness Rz of the support is from 5 to 200 μm, often from 20 to 100 μm (determined according to DIN 4768, Sheet 1, using a Hommel tester for DIN-ISO measured surface variables from Hommelwerke, Germany).

Furthermore, the support material may be porous or nonporous. The support material is expediently nonporous (total volume of the pores ≦1% by volume, based on the volume of the support).

The thickness of the active oxide material coat present on the coated catalyst is usually from 10 to 1000 mm. However, it may also be from 50 to 700 μm, from 100 to 600 μm or from 300 to 500 μm or from 150 to 400 μm. Possible coated thicknesses are also from 10 to 500 μm, from 100 to 500 μm or from 150 to 300 μm.

In principle, any desired geometries of the supports are suitable. Their longest dimension is as a rule from 1 to 10 mm. However, spheres or cylinders, in particular hollow cylinders (rings), are preferably used as supports. Advantageous diameters of the support spheres are from 1.5 to 4 mm. If cylinders are used as supports, their length is preferably from 2 to 10 mm and their external diameter preferably from 4 to 10 mm. In the case of rings, the wall thickness is moreover usually from 1 to 4 mm. Suitable annular supports can also have a length of from 3 to 6 mm, an external diameter of from 4 to 8 mm and a wall thickness of from 1 to 2 mm. However, an annular support having measurements of 7 mm×3 mm×4 mm or of 5 mm×3 mm×2 mm (external diameter x length x internal diameter) is also possible.

The preparation of the catalysts (III) can be carried out in a very simple manner by preforming active oxide materials of the formula (I), converting them into a finely divided form and finally applying them to the surface of the support with the aid of a liquid binder. For this purpose, the surface of the support is moistened in a very simple manner with the liquid binder and a coat of the active material is caused to adhere to the moistened surface by bringing said surface into contact with finely divided active oxide materials of the formula (I). Finally, the coated support is dried. Of course, the process can be repeated periodically to achieve a thicker coat. In this case, the coated parent structure becomes the new support, etc.

The fineness of the catalytically active oxide material of the formula (I) which is to be applied to the surface of the support is adapted to the desired coat thickness. For example, those active material powders of which at least 50% of the total number of powder particles pass through a sieve of mesh size of from 1 to 20 µm and whose numerical proportion of particles having a longest dimension above 50 µm is less than 10% are suitable for the coat thickness range of from 100 to 500 µm. As a rule, the distribution of the longest dimensions of the powder particles corresponds to a Gaussian distribution as a result of the preparation.

For carrying out the described coating process on an industrial scale, it is advisable, for example, to use the process principle disclosed in DE-A 29 096 71. There, the supports to be coated are initially taken in a preferably inclined (the angle of inclination is as a rule $\geq 0°$ and $\leq 90°$, in general $\geq 30°$ and $\leq 90°$; the angle of inclination is the angle of the central axis of the rotating container relative to the horizontal) rotating container (for example rotating pan or coating drum). The rotating container transports the supports, which for example are spherical or cylindrical, under two metering apparatuses arranged a specific distance apart. The first of the two metering apparatuses expediently corresponds to a nozzle (for example an atomizer nozzle operated with compressed air) through which the supports rolling in the rotating pan are sprayed and moistened in a controlled manner with the liquid binder. The second metering apparatus is located outside the atomization cone of the liquid binder sprayed in and serves for feeding in the finely divided oxidic active material (for example via a shaking conveyor or a powder screw). The support spheres moistened in a controlled manner take up the supplied active material powder which, as a result of the rolling movement, becomes compacted to a cohesive coat on the outer surface of the support, which for example is cylindrical or spherical.

If required, the support provided with the basecoat in this manner passes through the spray nozzles again in the course of the subsequent revolution, is moistened in a controlled manner in order to be able to take up a further coat of finely divided oxidic active material in the course of the further movement, etc. (intermediate drying is as a rule not necessary). Finely divided oxidic acid material and liquid binder are as a rule fed in continuously and simultaneously.

The liquid binder can be removed after the end of the coating, for example by the action of hot gases, such as $N_2$ or air. The coating process described is known to provide satisfactory adhesion both of the successive coats to one another and of the basecoat to the surface of the support.

What is important for the coating procedure described above is that the moistening of the support surface to be coated is carried out in a controlled manner. Briefly, this means that the support surface is expediently moistened so that it has adsorbed liquid binder but no liquid phase as such is visible on the support surface. If the support surface is too moist, the finely divided catalytically active oxide material forms separate agglomerates instead of being deposited on the surface. Detailed information in this context is to be found in DE-A 29 09 671.

The abovementioned final removal of the liquid binder used can be effected in a controlled manner, for example by evaporation and/or sublimation. In the simplest case, this can be effected by the action of hot gases of corresponding temperature (frequently from 50 to 300° C., often 150° C.). However, only preliminary drying can be effected by the action of hot gases. The final drying can then be carried out, for example, in a drying oven of any desired type (for example a belt dryer) or in the reactor. The temperature employed should not be above the calcination temperature used for the preparation of the oxidic active material. Of course, the drying can also be carried out exclusively in a drying oven.

Regardless of type and geometry of the support, the following can be used as binders for the coating process: water, monohydric alcohols, such as ethanol, methanol, propanol and butanol, polyhydric alcohols, such as ethylene glycol, 1,4-butanediol, 1,6-hexanediol or glycerol, monobasic or polybasic organic carboxylic acids, such as propionic acid, oxalic acid, malonic acid, glutaric acid or maleic acid, aminoalcohols, such as ethanolamine or diethanolamine, and monofunctional or polyfunctional organic amides, such as formamide. Advantageous binders are also solutions consisting of from 20 to 90% by weight of water and from 10 to 80% by weight of an organic compound which is dissolved in water and whose boiling point or sublimation temperature at atmospheric pressure (1 atm) is >100° C., preferably >150° C. The organic compound is advantageously selected from the above list of possible organic binders. Preferably, the organic fraction of the abovementioned aqueous binder solutions is from 10 to 50, particularly preferably from 20 to 30, % by weight. Other suitable organic components are monosaccharides and oligosaccharides, such as glucose, fructose, sucrose or lactose, and polyethylene oxides and polyacrylates.

The preparation of the catalytically active oxide materials of the formula (I) can be carried out in a manner known per se, as in the prior art publications cited above, i.e. the preparation can be carried out, for example, both hydrothermally and in a conventional manner.

In the latter case, the catalytically active oxide materials of the formula (I) are obtainable by producing from suitable sources of their elemental constituents a very intimate, preferably finely divided dry blend and subjecting the latter to a thermal treatment at from 350 to 700° C. or from 400 to 650° C. or from 400 to 600° C. The thermal treatment can be effected as described above in the case of the multimetal oxide material (II). The thorough mixing of the starting compounds can also be carried out as described above in the case of multimetal oxide material (II).

Suitable sources of the elemental constituents when carrying out the above-described preparation procedure for the catalytically active oxide materials of the formula (I) are the starting compounds or sources described above in the case of the multimetal oxide material (I).

Coated catalysts which have the multimetal oxide material (II) as catalytically active oxide material of the formula (I) are particularly preferred.

However, the active oxide materials of the formula (I) from WO 00/29106, which substantially have an amorphous structure which appears in the X-ray diffraction pattern in the form of very broad reflections having peaks at the 2θ angles of about 22° and about 27°, are also suitable for producing the coated catalysts.

However, the active oxide materials of the formula (I) from EP-A-0 529 853 and from EPA-0 608 838, which have very narrow reflections at 2θ peak positions of 22.1±0.3°, 28.2±0.3°, 36.2±0.3°, 45.2±0.3° and 50.0±0.3° in the X-ray diffraction pattern, are also suitable.

The coated catalysts can be prepared not only by applying the finished, finely milled active oxide materials of the formula (I) to the moistened support surface; instead of the active oxide material, a finely divided precursor material thereof can also be applied to the moistened support surface (using the same coating process and binder) and the calcination can be carried out after drying of the coated support. A suitable finely divided precursor material of this type is, for example, the material which is obtainable by first producing, from the sources of the elemental constituents of the desired active oxide material of the formula (I), a very intimate, preferably finely divided, dry blend (for example by spray-drying an aqueous suspension or solution of the sources) and subjecting this finely divided dry blend (if necessary after pelleting with addition of from 0.5 to 2% by weight of finely divided graphite) to a thermal treatment for a few hours at from 150 to 350° C., preferably from 250 to 350° C. under an oxidizing (oxygen-containing) atmosphere (for example under air) and, if required, finally subjecting it to milling. After the coating of the supports with the precursor material, calcination is then effected, preferably under an inert gas atmosphere (all other atmospheres are also suitable) at from 360 to 700° C. or from 400 to 650° C. or from 400 to 600° C.

The multimetal oxide materials (II) described above or the catalysts (III) comprising the multimetal oxide material (II) as the catalytically active oxide material can also be used for the oxidation of propene. Here, the propene can be oxidized in the presence of propane. If propane is used as a diluent gas, some of it can also be oxidized to acrylic acid.

The procedure for the propane oxidation is not subject to any restrictions. It can be carried out according to all processes known to a person skilled in the art. For example, the procedure described in EP-A-0 608 838 or WO 00/29106 can be employed, i.e. a gas B with which the catalyst is to be loaded at reaction temperatures of, for example, from 200 to 550° C. or from 230 to 480° C. or from 300 to 440° C. in step (c) may have, for example, the following composition:
from 1 to 15, preferably from 1 to 7, % by volume of propane,
from 44 to 99% by volume of air and
from 0 to 55% by volume of steam.

Other possible compositions of the gas mixture fed to step (c) for producing the gas B are:
from 70 to 95% by volume of propane,
from 5 to 30% by volume of molecular oxygen and
from 0 to 25% by volume of steam.

The plate-type heat exchanger reactors described in DE-A 199 52 964 are also suitable for carrying out the propane oxidation. In another embodiment of the present invention, the propane oxidation is carried out according to the processes described in DE-A 198 37 517, DE-A 198 37 518, DE-A 198 37 519 and DE-A 198 37 520.

The product gas mixture leaving the propene oxidation and/or propane oxidation as step (c) of the novel process does not exclusively consist of the desired product acrolein and/or acrylic acid but is as a rule composed substantially of acrolein and/or acrylic acid, unconverted molecular oxygen, propane, propene, molecular nitrogen, steam formed as a byproduct and/or concomitantly used as diluent gas, oxides of carbon which are formed as a byproduct and/or concomitantly used as diluent gas, and small amounts of other lower aldehydes, hydrocarbons and other inert diluent gases.

The desired product acrolein and/or acrylic acid can be separated from the product gas mixture in a manner known per se, for example by azeotropic separation, fractional distillation (with or without a solvent) or crystallization. For example, partial condensation of the acrylic acid, absorption of acrylic acid in water or in a high-boiling hydrophobic organic solvent or absorption of acrolein in water or in aqueous solutions of lower carboxylic acids with subsequent working-up of the absorbates is suitable; alternatively, the product gas mixture can also be subjected to fractional condensation, cf. for example EP-A-0 117 146, DE-A 43 08 087, DE-A 43 35 172, DE-A 44 36 243, DE-A 199 24 532 and DE-A 199 24 533.

In a particularly preferred embodiment of the novel process, after step (c) has been carried out and the desired product isolated, unreacted propane and/or propene are then separated from the remaining gas mixture according to the invention in steps (a) and (b) and are recycled to step (c).

The gas mixture A used in step (a) of the novel process may also be a gas mixture which has the composition of a gas mixture which is obtainable by catalytic dehydrogenation of propane to propene. Here, the dehydrogenation can be effected by oxidation, i.e. by supplying oxygen, or without a supply of oxygen, in particular substantially without a supply of oxygen. In the dehydrogenation with a supply of oxygen, a distinction may be made between two cases. In one case, all hydrogen formed is oxidized by an excess of oxygen so that the product gas no longer contains any hydrogen but excess oxygen (oxidative dehydrogenation). In the second case, only sufficient oxygen is added to cover the enthalpy of reaction, so that no oxygen is contained in the product gas but hydrogen may well be (autothermal procedure). The propane dehydrogenation can be carried out catalytically or homogeneously (noncatalytically).

Dehydrogenation of propane can be carried out, for example, as described in DE-A 33 13 573 and EP-A-0 117 146.

In principle, the oxidative propane dehydrogenation can be carried out as a homogeneous and/or heterogeneously catalyzed oxydehydrogenation of propane to propene with molecular oxygen. If this first reaction stage is designed as a homogeneous oxydehydrogenation, it can be carried out in principle as described, for example, in U.S. Pat. No. 3,798,283, CN-A-1 105 352, Applied Catalysis 70(2) (1991), 175-187, Catalysis Today 13 (1992), 673-678, and DE-A-196 22 331, it also being possible to use air as the oxygen source.

The temperature of the homogeneous oxydehydrogenation is expediently chosen to be in the range from 300 to 700° C., preferably from 400 to 600° C., particularly preferably from 400 to 500° C. The operating pressure may be from 0.5 to 100, in particular from 1 to 10, bar. The residence time is usually from 0.1 or 0.5 to 20, preferably from 0.1 or 0.5 to 5, seconds. The reactor used may be, for example, a tubular furnace or a tube-bundle reactor, for example a countercurrent tubular furnace with stack gas as a heat-transfer medium or tube-bundle reactor with salt melt as a heat-transfer medium. The propane-to-oxygen ratio in the starting mixture is preferably from 0.5:1 to 40:1, in particular from 1:1 to 6:1, more preferably from 2:1 to 5:1. The starting mixture may also comprise further, substantially inert, components, such as water, carbon dioxide, carbon monoxide, nitrogen, noble gases and/or propene, it also being possible for these to be recycled components. Here, components recycled to stage (a) are generally referred to as recycle gas.

If the propane dehydrogenation is designed as a heterogeneously catalyzed oxydehydrogenation, it can be carried out in principle as described, for example, in U.S. Pat. No. 4,788,371, CN-A 1073893, Catalysis Letters 23 (1994), 103-106, W. Zhang, Gaodeng Xuexiao Huaxue Xuebao 14 (1993), 566, Z. Huang, Shiyou Huagong 21 (1992), 592, WO 97/36849, DE-A 197 53 817, U.S. Pat. No. 3,862,256, U.S. Pat. No. 3,887,631, DE-A 195 30 454, U.S. Pat. No. 4,341,664, J. of Catalysis 167 (1997), 560-569, J. of Catalysis 167 (1997), 550-559, Topics in Catalysis 3 (1996), 265-275, U.S. Pat. No. 5,086,032, Catalysis Letters 10 (1991), 181-192, Ind. Eng. Chem. Res. 35 (1996), 14-18, U.S. Pat. No. 4,255,284, Applied Catalysis A: General 100 (1993), 111-130, J. of Catalysis 148 (1994), 56-67, V. Cortés Corberán and S. Vic Belló(Ed.), New Developments in Selective Oxidation II, 1994, Elsevier Science B.V., pages 305-313, 3$^{rd}$ World Congress on Oxidation Catalysis, R. K. Grasselli, S. T. Oyama, A. M. Gaffney and J. E. Lyons (Ed.), 1997, Elsevier Science B.V., page 375 et seq. Air may also be used as the oxygen source. Preferably, however, the oxygen source comprises at least 90, more preferably 95, mol %, based on 100 mol % of the oxygen source, of oxygen.

The catalysts suitable for the heterogeneous oxydehydrogenation are not subject to any particular restrictions. All oxydehydrogenation catalysts which are known to a person skilled in the art in this area and which are capable of oxidizing propane to propene are suitable. In particular, all oxydehydrogenation catalysts stated in the abovementioned publications may be used. Preferred catalysts include, for example, oxydehydrogenation catalysts which comprise MoVNb oxides or vanadyl pyrophosphate, each with a promoter. An example of a particularly suitable catalyst is a catalyst which contains a mixed metal oxide comprising Mo, V, Te, O and X as substantial components, where X is at least one element selected from niobium, tantalum, tungsten, titanium, aluminum, zirconium, chromium, manganese, iron, ruthenium, cobalt, rhodium, nickel, palladium, platinum, antimony, bismuth, boron, indium and cerium. Other particularly suitable oxydehydrogenation catalysts are the multimetal oxide materials or multimetal oxide catalysts A of DE-A-197 53 817, the multimetal oxide materials or multimetal oxide catalysts A stated in the abovementioned publication as being preferred being very particularly advantageous. This means that particularly suitable active materials are multimetal oxide materials (IV) of the formula IV

$$M^1{}_aMO_{1-b}M^2{}_bO_x \qquad (IV),$$

where

M$^1$ is Co, Ni, Mg, Zn, Mn and/or Cu,
M$^2$ is W, V, Te, Nb, P, Cr, Fe, Sb, Ce, Sn and/or La,
a is 0.5-1.5
b is 0-0.5 and x is a number which is determined by the valency and frequency of the elements other than oxygen in (IV).

In principle, suitable active materials (IV) can be prepared in a simple manner by producing, from suitable sources of their elemental constituents, a very intimate, preferably finely divided, dry blend having a composition corresponding to their stoichiometry and calcining this dry blend at from 450 to 1000° C. Suitable sources of the elemental constituents of the multimetal oxide active materials (IV) are those compounds which are oxides and/or those compounds which can be converted into oxides by heating, at least in the presence of oxygen. These are in particular halides, nitrates, formates, oxalates, citrates, acetates, carbonates, ammine complex salts, ammonium salts and/or hydroxides. The thorough mixing of the starting compounds for the preparation of the multimetal oxide materials (IV) can be effected in dry form, for example as finely divided powder, or in wet form, for example using water as a solvent. The multimetal oxide materials (IV) can be used both in powder form and after shaping to give specific catalyst geometries, it being possible to carry out the shaping before or after the final calcination. Unsupported catalysts may be used, or the shaping of a pulverulent active material or precursor material can also be effected by application to preshaped inert catalyst supports. Conventional, porous or nonporous aluminas, silica, thorium dioxide, zirconium dioxide, silicon carbide or silicate can be used as support materials, it being possible for the supports to have a regular or irregular shape.

For the heterogeneously catalyzed oxydehydrogenation of propane, the reaction temperature is preferably from 200 to 600° C., in particular from 250 to 500° C., more preferably from 350 to 440° C. The operating pressure is preferably from 0.5 to 10, in particular from 1 to 10, more preferably from 1 to 5, bar. Operating pressures above 1 bar, for example from 1.5 to 10 bar, have proven particularly advantageous. As a rule, the heterogeneously catalyzed oxydehydrogenation of propane is carried out over a fixed catalyst bed. The latter is expediently loaded into the tubes of a tube-bundle reactor, as described, for example, in EP-A-0 700 893 and in EP-A-0 700 714 and the literature cited in these publications. The average residence time of the reaction gas mixture in the catalyst bed is expediently from 0.5 to 20 seconds. The ratio of propane to oxygen varies with the desired conversion and the selectivity of the catalyst and is expediently from 0.5:1 to 40:1, in particular from 1:1 to 6:1, more preferably from 2:1 to 5:1. As a rule, the propene selectivity decreases with increasing propane conversion. The propane-to-propene reaction is therefore preferably carried out in such a way that relatively low propane conversions are achieved in combination with high propene selectivity. The propane conversion is particularly preferably from 5 to 40%, more preferably from 10 to 30%. Here, the term propane conversion means the proportion of supplied propane which is converted. The selectivity is particularly preferably from 50 to 98%, more preferably from 80 to 98%, the term selectivity referring to the number of moles of propene which are produced per mole of converted propane, expressed as a percentage.

Preferably, the starting mixture used in the oxidative propane dehydrogenation contains from 5 to 95% by weight, based on 100% by weight of starting mixture, of propane. In addition to propane and oxygen, the starting mixture for the heterogeneously catalyzed oxydehydrogenation may also comprise further, in particular inert, components, such as water, carbon dioxide, carbon monoxide, nitrogen, noble gases and/or propene. The heterogeneous oxydehydrogenation can also be carried out in the presence of diluents, for example steam.

Any desired reactor sequence which is known to a person skilled in the art may be used for carrying out the homogeneous oxydehydrogenation or the heterogeneously catalyzed oxydehydrogenation. For example, the reaction can be carried out in a single stage or in two or more stages between which oxygen is introduced. It is also possible to use homogeneous and heterogeneously catalyzed oxydehydrogenations in combination with one another.

As possible constituents, the product mixture of the propane oxydehydrogenation may contain, for example, the following components: propene, propane, carbon dioxide, carbon monoxide, water, nitrogen, oxygen, ethane, ethene, methane, acrolein, acrylic acid, ethylene oxide, butane, acetic acid, formaldehyde, formic acid, propylene oxide and butene. A preferred product mixture obtained in the propane oxydehydrogenation contains: from 5 to 10% by weight of propene, from 1 to 2% by weight of carbon monoxide, from 1 to 3% by weight of carbon dioxide, from 4 to 10% by weight of water, from 0 to 1% by weight of nitrogen, from 0.1 to 0.5% by weight of acrolein, from 0 to 1% by weight of acrylic acid, from 0.05 to 0.2% by weight of acetic acid, from 0.01 to 0.05% by weight of formaldehyde, from 1 to 5% by weight of oxygen, from 0.1 to 1.0% by weight of further abovementioned components and propane as the remainder, based in each case on 100% by weight of product mixture.

In general, the propane dehydrogenation for the preparation of gas mixture A can also be carried out as a heterogeneously catalyzed propane dehydrogenation substantially in the absence of oxygen, as described in DE-A 33 13 573, or as follows.

Since the dehydrogenation reaction takes place with an increasing volume, the conversion can be increased by reducing the partial pressure of the products. This can be achieved in a simple manner, for example by dehydrogenation at reduced pressure and/or by admixing of substantially inert diluent gases, for example steam, which is usually an inert gas for the dehydrogenation reaction. Another advantage of dilution with steam is that it generally results in reduced coking of the catalyst used since the steam reacts with resulting coke according to the principle of gasification of coal. Moreover, steam may be present as diluent gas in the downstream oxidation step (c). However, steam can also easily be separated off partly or completely before step (a) (for example by condensation), which makes it possible to increase the proportion of diluent gas $N_2$ when the gas mixture obtainable thereby is further used in oxidation step (c). Further diluents suitable for the propane dehydrogenation are, for example, CO, $CO_2$, nitrogen and noble gases, such as He, Ne and Ar. All diluents stated may be present either by themselves or in the form of a very wide range of mixtures. It is advantageous that said diluents are as a rule also diluents suitable for the oxidation step (c). In general, diluents which are inert in the respective stage (i.e. which undergo chemical change to an extent of less than 5, preferably less than 3 and more preferably less than 1, mol %) are preferred. In principle, all dehydrogenation catalysts known in the prior art are suitable for the propane dehydrogenation. They can be divided roughly into two groups, i.e. into those which are oxidic in nature (for example chromium oxide and/or alumina) and those which consist of at least one, as a rule comparatively noble, metal (for example platinum) deposited on a generally oxidic support.

Inter alia, all dehydrogenation catalysts which are recommended in WO 99/46039, U.S. Pat. No. 4, 788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105 and DE-A 199 37 107 can thus be used. In particular, the catalyst according to example 1, example 2, example 3 and example 4 of DE-A 199 37 107 can be used.

These are dehydrogenation catalysts which contain from 10 to 99.9% by weight of zirconium dioxide, from 0 to 60% by weight of alumina, silica and/or titanium dioxide and from 0.1 to 10% by weight of at least one element of the first or second main group, one element of the third subgroup, one element of the eighth subgroup of the Periodic Table of the Elements, lanthanum and/or tin, with the proviso that the sum of the percentages by weight is 100% by weight.

In principle, all reactor types and process variants known in the prior art are suitable for carrying out the propane dehydrogenation. Descriptions of such process variants are contained, for example, in all prior art publications mentioned in relation to the dehydrogenation catalysts.

A comparatively detailed description of dehydrogenation processes suitable according to the invention is also contained in Catalytical Studies Division, Oxidative Dehydrogenation and Alternative Dehydrogenation Processes, Study Number 4192 OD, 1993, 430 Ferguson Drive, Mountain View, Calif., 94043-5272 U.S.A.

Typical of partial heterogeneously catalyzed dehydrogenation of propane is that it takes place endothermically, i.e. the heat (energy) necessary for establishing the required reaction temperature must be supplied either to the reaction gas beforehand and/or in the course of the catalytic dehydrogenation.

Furthermore, owing to the high reaction temperatures required, it is typical of heterogeneously catalyzed dehydrogenations of propane that small amounts of high-boiling high molecular weight organic compounds, including carbon, are formed and are deposited on the catalyst surface and thus deactivate the latter. In order to minimize this disadvantageous phenomenon, the propane to be passed over the catalyst surface for the catalytic dehydrogenation at elevated temperatures can be diluted with steam. Under the resulting conditions, carbon deposited is partly or completely eliminated by the principle of the gasification of coal.

Another possibility for eliminating deposited carbon compounds is to pass an oxygen-containing gas through the dehydrogenation catalyst from time to time at elevated temperatures and thus more or less to burn off the deposited carbon. Suppression of the formation of carbon deposits is however also possible by adding molecular hydrogen to the propane to be dehydrogenated catalytically, before it is passed at elevated temperatures over the dehydrogenation catalyst.

Of course, it is also possible to add steam and molecular hydrogen as a mixture to the propane to be dehydrogenated catalytically. The addition of molecular hydrogen to the catalytic dehydrogenation of propane also reduces the undesired formation of allene and acetylene as byproducts.

A suitable reactor form for the propane dehydrogenation is the fixed-bed tubular reactor or tube-bundle reactor. This means that the dehydrogenation catalyst is present as a fixed bed in a reaction tube or in a bundle of reaction tubes. The reaction tubes are heated by combustion of a gas, for example a hydrocarbon, such as methane, in the space surrounding the reaction tubes. It is advantageous to use this direct form of catalyst tube heating only over the initial about 20 to 30% of the fixed bed and to heat up the remaining bed length to the required reaction temperature by the radiant heat liberated in the course of the combustion. In this way, an almost isothermal reaction is achievable. Suitable internal diameters of the reaction tubes are from about 10 to 15 cm. A typical dehydrogenation tube-bundle reactor comprises from 300 to 1000 reaction tubes. The temperature in the interior of the reaction tube is from 300 to 700° C., preferably from 400 to 700° C. Advantageously, the reaction gas is preheated to the reaction temperature before being fed to the tubular reactor. Frequently, the product gas mixture leaves the reaction tube at a temperature of from 50 to 100° C. lower. In the abovementioned procedure, the use of oxidic dehydrogenation catalysts based on chromium oxide and/or alumina is expedient.

Frequently, no diluent gas is present but substantially pure propane is employed as starting reaction gas. The dehydrogenation catalyst, too, is generally used undiluted.

On the industrial scale, about three tube-bundle reactors would be operated in parallel. Two of these reactors would as a rule be in the dehydrogenation mode while the catalyst load is regenerated in one of the reactors.

The above procedure is used, for example, in the BASF Linde propane dehydrogenation process known in the literature.

Furthermore, it is used in the steam active reforming (STAR) process which was developed by Phillips Petroleum Co. (cf. for example U.S. Pat. No. 4,902,849, U.S. Pat. No. 4,996,387 and U.S. Pat. No. 5,389,342). The dehydrogenation catalyst used in the STAR process is advantageously promoter-containing platinum on zinc (magnesium) spinel as a support (cf. for example U.S. Pat. No. 5,073,662). In contrast to the BASF Linde propane dehydrogenation process, propane to be dehydrogenated in the STAR process is diluted with steam. A molar ratio of steam to propane in the range of from 4 to 6 is typical. The operating pressure is frequently from 3 to 8 atom and the reaction temperature is expediently chosen to be from 480 to 620° C. Typical catalyst loadings with the total reaction gas mixture are from 0.5 to 10 h$^{-1}$.

The propane dehydrogenation can also be designed in the form of a moving bed. For example, the moving catalyst bed can be housed in a radial flow reactor. The catalyst moves therein slowly from top to bottom while the reaction gas mixture flows radially. This procedure is used, for example, in the UOP Oleflex dehydrogenation process. Since the reactors in this process are operated quasi-adiabatically, it is expedient to operate a plurality of reactors connected in series (typically up to four). This makes it possible to avoid excessively large differences in the temperatures of the reaction gas mixture at the reactor entrance and at the reactor exit (in the case of the adiabatic mode of operation, the reaction gas starting mixture acts as a heat-transfer medium on whose heat content the reaction temperature is dependent) and nevertheless to achieve attractive total conversions.

When the catalyst bed has left the moving-bed reactor, it is regenerated and then reused. For example, a spherical dehydrogenation catalyst which substantially comprises platinum on spherical alumina supports can be used as a dehydrogenation catalyst for this process. In the UOP variant, hydrogen is added to the propane to be dehydrogenated, in order to avoid premature catalyst aging. The operating pressure is typically from 2 to 5 atm. The molar hydrogen-to-propane ratio is expediently from 0.1 to 1. The reaction temperatures are preferably from 550 to 650° C. and the time for which the catalyst is in contact with the reaction gas mixture is chosen to be from about 2 to 6 h$^{-1}$.

In the fixed-bed process described, the catalyst geometry may likewise be spherical or cylindrical (hollow or solid).

As a further process variant for the propane dehydrogenation, Proceedings De Witt, Petrochem. Review, Houston, Tex., 1992 a, N1, describes the possibility of heterogeneously catalyzed propane dehydrogenation in a fluidized bed, in which the propane is not diluted.

Expediently, two fluidized beds are operated side by side, one of which is as a rule present in the regeneration state. The active material used is chromium oxide on alumina. The operating pressure is typically from 1 to 1.5 atm and the dehydrogenation temperature is as a rule from 550 to 600° C. The heat required for the dehydrogenation is introduced into the reaction system by preheating the dehydrogenation catalyst to the reaction temperature. The operating pressure is usually from 1 to 2 atm and the reaction temperature is typically from 550 to 600° C. The above dehydrogenation procedure is also known in the literature as the Snamprogetti-Yarsintez process.

As an alternative to the procedures described above, the heterogeneously catalyzed propane dehydrogenation in the substantial absence of oxygen can also be realized according to a process developed by ABB Lummus Crest (cf. Proceedings De Witt, Petrochem. Review, Houston, Tex., 1992, P1). The heterogeneously catalyzed propane dehydrogenation processes in the substantial absence of oxygen which have been described to date have in common the fact that they are operated at propane conversions of >30 mol % (as a rule ≦60 mol %) (based on a single reactor pass). It is advantageous that it is sufficient to achieve a propane conversion of from ≧5 to ≦30 or ≦25 mol %. This means that the propane dehydrogenation can also be operated at propane conversions of from 10 to 20 mol % (the conversions are based on a single reactor pass). This is due, inter alia, to the fact that the remaining amount of unconverted propane is diluted in the downstream oxidation step (c) with molecular nitrogen, which reduces the propionaldehdye and/or propionic acid byproduct formation.

For realizing the abovementioned propane conversions, it is advantageous to carry out the propane dehydrogenation at an operating pressure of from 0.3 to 3 atm. It is also advantageous to dilute the propane to be dehydrogenated with steam. Thus, on the one hand, the heat capacity of the water makes it possible to compensate some of the effect of the endothermic nature of the dehydrogenation and, on the other hand, the dilution with steam reduces the partial pressure of starting materials and products, which has an advantageous effect on the equilibrium position of the dehydrogenation. Furthermore, as stated above, the presence of steam has an advantageous effect on the time-on-stream of the dehydrogenation catalyst. If required, molecular hydrogen may also be added as a further component. The molar ratio of molecular hydrogen to propane is as a rule <5. With a comparatively low propane conversion, the molar ratio of steam to propane can accordingly be from >0 to 30, expediently from 0.1 to 2, advantageously from 0.5 to 1. The fact that only a comparatively small amount of heat is consumed in a single reactor pass of the reaction gas and comparatively low reaction temperatures are sufficient for achieving the conversion in a single reactor pass proves to be advantageous for a procedure having a low propane conversion.

It may therefore be expedient to carry out the propane dehydrogenation (quasi) adiabatically with a comparatively low propane conversion, i.e. the reaction gas starting mixture is heated as a rule to a temperature of from 500 to 700° C. (for example by direct firing of the surrounding wall) or from 550 to 650° C. Usually, a single adiabatic pass through a catalyst bed is then sufficient to achieve the desired conversion, the reaction gas mixture being cooled by from about 30 to 200° C. (depending on conversion). The presence of steam as a heat-transfer medium is advantageous even from the point of view of an adiabatic procedure. The lower reaction temperature permits longer times-on-stream of the catalyst bed used.

In principle, the propane dehydrogenation with comparatively low propane conversion, whether adiabatically or isothermally operated, can be carried out both in a fixed-bed reactor and in a moving-bed or fluidized-bed reactor.

It is noteworthy that a single shaft furnace reactor in the form of a fixed-bed reactor through which the reaction gas mixture flows axially and/or radially is sufficient for realizing said dehydrogenation, in particular in adiabatic operation.

In the simplest case, this is a single closed reaction volume, for example a container, whose internal diameter is from 0.1 to 10 m, possibly also from 0.5 to 5 m, and in which the catalyst bed is installed on a support apparatus (for example a grille). The reaction volume which is loaded with catalyst and is heat-insulated in adiabatic operation is flowed through axially by the hot, propane-containing reaction gas. The catalyst geometry may be spherical, annular or strand-like. Since in this case the reaction volume is to be realized by a very economical apparatus, all catalyst geometries which have a particularly low pressure drop are preferable. These are in particular catalyst geometries which lead to a large cavity volume or are built up in a structured manner, for example honeycombs. In order to realize radial flow of the propane-containing reaction gas, the reactor may consist, for example, of two cylindrical grilles present in a casing and mounted concentrically one inside the other, and the catalyst bed may be arranged in their annular gap. In the adiabatic case, the metal casing in turn would be thermally insulated.

The catalysts disclosed in DE-A 199 37 107, especially all those disclosed by way of example, are particularly suitable as a catalyst load for the propane dehydrogenation with comparatively low propane conversion in a single pass.

After a relatively long operating time, the abovementioned catalysts can be regenerated, for example, in a simple manner by passing air diluted with nitrogen over the catalyst bed at from 300 to 600° C., frequently from 400 to 500° C., initially in the first regeneration stages. The catalyst loading with regeneration gas may be, for example, from 50 to 10000 h$^{-1}$ and the oxygen content of the regeneration gas may be from 0.5 to 20% by volume.

In further downstream regeneration stages, air can be used as regeneration gas under otherwise identical regeneration conditions. It is expedient in application technology to flush the catalyst with inert gas (for example $N_2$) before its regeneration.

Thereafter, it is generally advisable to effect regeneration with pure molecular hydrogen or with molecular hydrogen diluted with inert gas (the hydrogen content should be ≧1% by volume) under an otherwise identical range of conditions.

The propane dehydrogenation with comparatively low propane conversion (≦30 mol %) can be operated in all cases at the same catalyst loadings (relating both to the reaction gas as a whole and the propane contained therein) as the variants with high propane conversion (>30 mol %). This loading with reaction gas may be, for example, from 100 to 10000 h$^{-1}$, frequently from 100 to 3000 h$^{-1}$, i.e. often from about 100 to 2000 h$^{-1}$.

The propane dehydrogenation with comparatively low propane conversion can be realized in a particularly elegant manner in a tray reactor.

This contains, spatially in succession, more than one catalyst bed catalyzing the dehydrogenation. The number of catalyst beds may be from 1 to 20, expediently from 2 to 8, but also from 3 to 6. The catalyst beds are preferably arranged radially or axially one behind the other. In terms of application technology, it is expedient to use the fixed catalyst bed type in such a tray reactor.

In the simplest case, the fixed catalyst beds in a shaft furnace reactor are arranged axially or in the annular gaps of cylindrical grilles installed concentrically one inside the other. However, it is also possible to arrange the annular gaps in segments and, after radial passage through a segment, to pass the gas into the next segment above or below.

Expediently, the reaction gas mixture is subjected to intermediate heating in the tray reactor on its way from one catalyst bed to the next catalyst bed, for example by passing it over heat exchanger ribs heated with hot gases or by passing it through pipes heated with hot combustion gases.

If the tray reactor is otherwise operated adiabatically, it is sufficient for the desired propane conversions (≦30 mol %), particularly with the use of the catalysts described in DE-A 199 37 107, in particular the exemplary embodiments, to preheat the reaction gas mixture to a temperature from 450 to 550° C. before passing it into the dehydrogenation reactor and to keep it within this temperature range inside the tray reactor. This means that the total propane dehydrogenation is thus to be realized at extremely low temperatures, which proves to be particularly advantageous for the time-on-stream of the fixed catalyst beds between two regenerations.

It is even more elegant to carry out the intermediate heating described above by a direct method (autothermal procedure). For this purpose, a limited amount of molecular oxygen is added to the reaction gas mixture, before it flows through the first catalyst bed and/or between the downstream catalyst beds. Depending on the dehydrogenation catalyst used, limited combustion of the hydrocarbons contained in the reaction gas mixture, any coke deposited on the catalyst surface or coke-like compounds and/or hydrogen formed in the course of the propane dehydrogenation and/or added to the reaction gas mixture is thus effected (it may also be expedient in terms of application technology to introduce into the tray reactor catalyst beds which are loaded with catalyst which specifically (selectively) catalyzes the combustion of hydrogen (and/or of hydrocarbon) (suitable catalysts of this type are, for example, those of U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, such catalyst beds can be housed in the tray reactor so as to alternate with the beds containing the dehydrogenation catalyst)). The heat of reaction evolved thus permits virtually isothermal operation of the heterogeneously catalyzed propane dehydrogenation in a quasiautothermal manner. As the chosen residence time of the reaction gas in the catalyst bed increases, a propane dehydrogenation with decreasing or substantially constant temperature is possible, which permits particularly long times-on-stream between two regenerations.

As a rule, an oxygen feed as described above should be effected so that the oxygen content of the reaction gas mixture is from 0.5 to 10% by volume, based on the amount of propane and propene contained therein. Suitable oxygen sources are both pure molecular oxygen and oxygen diluted with inert gas, for example CO, $CO_2$, $N_2$ or noble gases, in particular air. The resulting combustion gases generally have an additional diluting effect and thus promote the heterogeneously catalyzed propane dehydrogenation.

The isothermal nature of the heterogeneously catalyzed propane dehydrogenation can be further improved by mounting closed internals (for example annular ones), advantageously but not necessarily evacuated, in the spaces between the catalyst beds in the tray reactor before they are introduced. Such internals may also be placed in the respective catalyst bed. These internals contain suitable solids or liquids which evaporate or melt above a specific temperature and thus consume heat and condense and thereby liberate heat where the temperature falls below this temperature.

One possibility of heating the reaction gas mixture to the required reaction temperature in the propane dehydrogenation is also to combust a part of the propane and/or $H_2$ contained therein by means of molecular oxygen (for example, over suitable combustion catalysts having a specific action, for example by simply passing over and/or passing through) and to effect heating to the desired reaction temperature by means of the heat of combustion thus liberated. The resulting combustion products, such as $CO_2$ and $H_2O$, and any $N_2$ accompanying the molecular oxygen required for the combustion advantageously form inert diluent gases.

According to the invention, it is also possible for propane unconverted and optionally propene after carrying out step (c) and separating off the desired product (acrolein and/or acrylic acid) to be subjected to propane dehydrogenation, which can be carried out as described above, and for the product gas mixture obtained after the propane dehydrogenation to be subjected again to step (a).

Where a propane dehydrogenation is carried out, propane is a possible diluent gas in step (c).

It is also possible to add, in particular when a propane dehydrogenation is carried out, to gas B supplied to step (c) still pure propane and/or propene.

If step (c) is carried out as a conversion of propene to acrylic acid, then the exit gas from the working-up also contains oxidizable secondary components, for example carbon monoxide, formic acid, formaldehyde, acetic acid and small amounts of acrylic acid in addition to the components not converted in the oxidation, i.e. propane, nitrogen and residual oxygen. In a particularly preferred embodiment, these secondary components are catalytically oxidized before a propane dehydrogenation with the residual oxygen and, if required, with additional molecular oxygen, in order to heat up the gas before the dehydrogenation. This oxidation could be carried out in a postcombustion catalyst, such as a Pd catalyst on an alumina support, for example RO-20/13 or RO-20/25 (both from BASF).

Preferred embodiments of the invention are shown in FIGS. 1 to 7 described below, which illustrate the invention without restricting it.

FIGS. 1 to 5 show schematic diagrams for carrying out preferred processes, in which, for simplification, not all feed and discharge streams are shown. FIG. 1 shows an absorption and desorption stage 1, an oxidation stage 2, which is in the form of an oxidation of propene to acrolein and/or acrylic acid, and a working-up stage 3. In FIG. 1, propane and propene, if required with residual amounts of nitrogen, are absorbed into a suitable absorbent in stage 1 from a mixture which contains propane, propene, hydrogen and oxides of carbon (carbon monoxide and carbon dioxide) and possibly nitrogen and further hydrocarbons, and are desorbed from said absorbent by stripping with air. In this way, hydrogen, the oxides of carbon, further hydrocarbons and nitrogen are removed. The stream containing propene and possible propane is then fed to the oxidation stage 2, in which propene is oxidized to acrolein and/or acrylic acid. After the oxidation 2, the product obtained is fed to the working-up 3. There, the desired products acrolein and/or acrylic acid are isolated. The remaining unconverted propene and propane and oxides of carbon and any residues of nitrogen and oxygen are once again fed to the absorption and desorption stage 1.

In the further figures, identical reference numerals denote the same as in FIG. 1.

Figure 2:
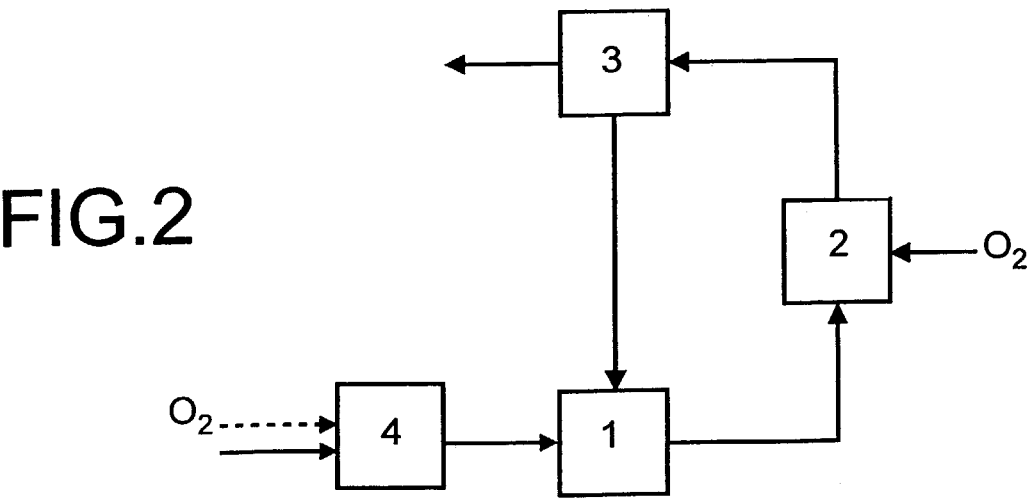

In contrast to FIG. 1, in FIG. 2 a propane dehydrogenation 4 is installed upstream and can be carried out with or without a supply of oxygen. The gas mixture obtained in the propane dehydrogenation and containing hydrogen, oxides of carbon and possibly residues of nitrogen and hydrocarbons in addition to the propane and the propene is fed to the absorption and desorption stage 1.

Figure 3:
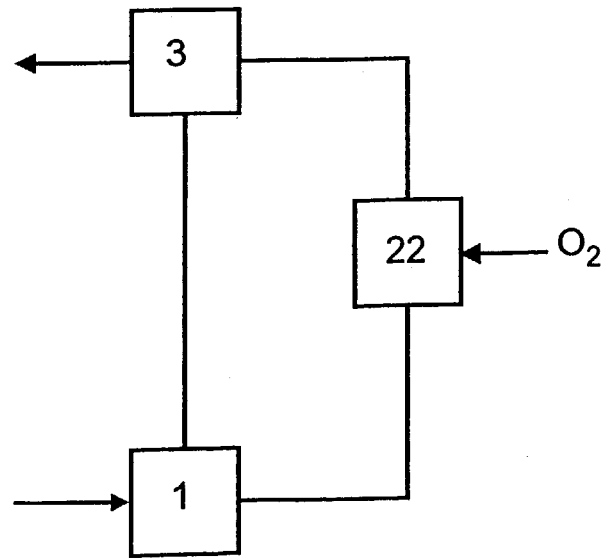

In contrast to FIG. 1, in FIG. 3 a propane oxidation stage 22, in which propane is oxidized to acrolein and/or acrylic acid, is present instead of propene oxidation 2.

Figure 4:
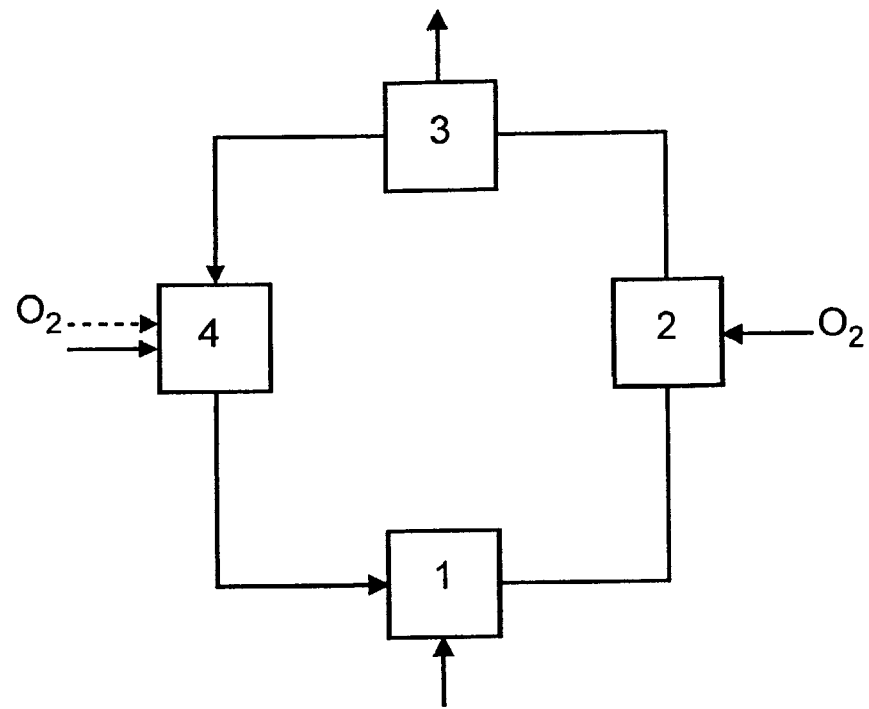

In FIG. 4, a propane dehydrogenation stage 4 with or without a supply of oxygen is carried out after the working-up stage 3 and the gas mixture obtained in this stage is recycled to the absorption and desorption stage 1.

Figure 5:
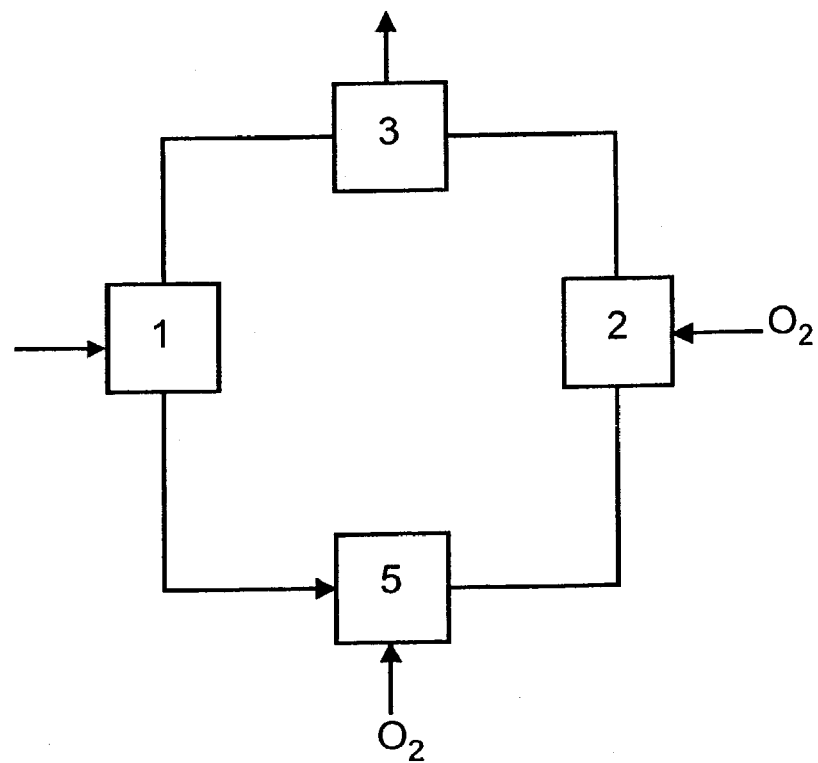

FIG. 5 shows a further preferred embodiment of the process, in which a propane dehydrogenation 5 with an oxygen supply is installed downstream of the absorption and desorption stage 1.

Figure 7:
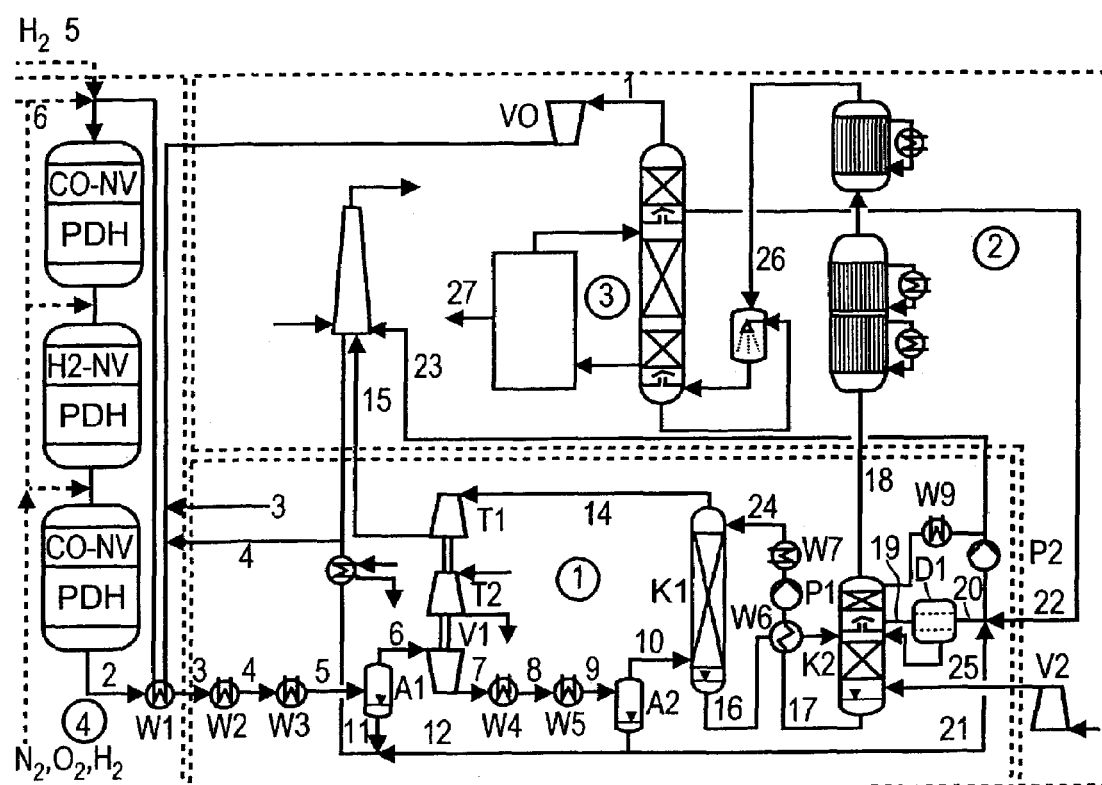

FIGS. 6 and 7 show further preferred processes. The process of FIG. 6 follows the process diagram of FIG. 4. In FIG. 4, three reactors are present in the propane dehydrogenation stage 4, in the first of which a carbon monoxide postcombustion (CO-PC) takes place before the propane dehydrogenation (PDH), while in the two downstream reactors a hydrogen postcombustion (H2-PC) takes place before the propane dehydrogenation (PDH). These postcombustions serve for supplying energy for the propane dehydrogenation. The number of reactors in the propane dehydrogenation is not limited to three reactors. In the propane dehydrogenation 4, propane is fed in via line (30). Air can be fed in via line (6). The gas mixture obtained after the propane dehydrogenation is fed via a heat exchanger W and a compressor V in stage 1 to an absorption column K1 and a desorption column K2. After the desorption in K2, the absorbent is recycled to absorption column K1. Unabsorbed gases are removed from the process as waste gas (33), if necessary via an incineration plant E. The stream containing separated off propane and/or propene is fed to the oxidation stage 2, which is shown here with four oxidation reactors. However, the number of oxidation reactors is not limited to this number. The desired product acrolein and/or acrylic acid is then worked up in stage 3 and is taken off via line (31). Unconverted propane and/or propene is recycled as recycle gas via line (32), together with the other gaseous components not separated off here in the absorption, to the propane dehydrogenation 4.

In FIG. 7, recycle gas (1) from the working-up stage 3, which gas is obtained at from 10 to 90° C. and from 0.8 to 5 bar and can be further compressed to pressures of from 2 to 10 bar, for example with the aid of a compressor V0, is heated, in a heat exchanger W1 countercurrently to the reaction gas (2) from the propane dehydrogenation (PDH) 4, to temperatures of from 100 to 650° C. In the case of FIG. 7, the stated pressure in bar relates here and below to absolute pressure.

Suitable compressors are all suitable embodiments which are known to a person skilled in the art and are mentioned in more detail below.

The recycle gas stream (1) contains from about 40 to 80% by volume of $N_2$, from about 1 to 5% by volume of $CO_2$, from 0.1 to 2% by volume of CO, from 2 to 5% by volume of $O_2$, from 0.5 to 25% by volume of $H_2O$, further oxidation byproducts and from about 5 to 40% by volume of unconverted propane and from about 0.1 to 3% by volume of unconverted propene. Before or after the heating-up, fresh propane (3) and preferably water or steam (4) are mixed with the gas before it is passed into the PDH 4. Suitable fresh propane is any available propane-containing gas or liquid. However, propane sources such as industrial propane (>90%, in particular >95%, particularly preferably >98%, propane content with a small $C_4^+$ fraction) or pure propane (>99% propane content) are advantageous. The molar ratio of water or steam to propane in the gas stream is from 0.05 to 5, preferably from 0.1 to 2. It may be advantageous to mix with this gas stream additionally $H_2$ (5), air (6) or an $O_2$-containing gas and further components capable of exothermic conversion in the PDH, for example CO or $CO/H_2$ mixtures, such as synthesis gas. The purity of these gases is not subject to any restriction. The exothermic nature of the oxidation of the combustible components in the PDH serves for covering the endothermic nature of the PDH reaction, so that less additional heat, and in the most advantageous case no additional heat has to be supplied from outside for covering the enthalpy of reaction for the PDH.

The PDH is operated at from 0.3 to 10, preferably from 1 to 5, bar and from 350 to 700° C., preferably from 400 to 600° C. Possible reactors for the PDH are all embodiments known to a person skilled in the art, for example axial-flow apparatuses, such as tray reactors, and also apparatuses having a plurality of catalyst beds which are arranged in the form of a hollow cylinder and having radial flow, or a plurality of individual apparatuses, for example column-type, cake-type or spherical apparatuses. The number of reactors in the PDH is not limited to 3. Preferably, a plurality of individual apparatuses is used since the intermediate feeding of further gases is possible in a simple manner thereby and moreover individual catalyst beds can be treated in a particular manner, for example regenerated, separately from the others during operation. For this purpose, for example, the reactor containing the catalyst bed to be regenerated is isolated from the main gas stream by suitable shut-off elements, for example slide valves, valves or flaps which are present in the connecting lines between the reactors, and the gases required for regeneration, for example $N_2$, $H_2$, lean air or air or $O_2$-rich gases, are then passed over the catalyst bed and deposits are removed from the catalyst. The remaining reactors, a total number of which may be from 1 to 20, preferably from 2 to 5, are still fed with the main gas stream and produce mainly the desired product propene.

In the PHD reactors, the catalyst layers may rest on grilles, beds of inert material or similar support apparatuses known to a person skilled in the art. The form of the catalyst is not subject to any restrictions. Forms such as chips, spheres, extrudates, rings, cylinders or structured packings and monoliths may be used. Those geometries which provide a small pressure drop are advantageous.

For the distribution of the gas fed in over the catalyst bed, gas distributors known to a person skilled in the art, for example sieve trays, ring distributors or manifolds, and irregular beds or structured packings, for example static mixers, may be used.

A plurality of catalyst layers having different functions may be arranged in the PDH reactors. If a plurality of catalyst layers are used, it is advantageous to arrange, before the PDH catalyst layer, one or more catalyst layers over which preferably, for example, $H_2$, CO and/or a further oxidizable component which is not propene or propane can be oxidized (CO—PC or $H_2$—PC). However, it is also possible to dispense with additional catalyst layers upstream of the PDH catalyst layer if the PDH catalyst performs this function or propane losses through oxidation with propane are economically acceptable.

The PDH catalysts can be operated with from 100 to 20000, preferably from 500 to 10000, more preferably from 1000 to 10000, l(S.T.P.) of propane per liter of catalyst bed per hour. The gas space velocity for catalysts which oxidize, for example, predominantly CO or $H_2$ and to a lesser extent propane or propene is usually from 5000 to 30000 l(S.T.P.) of gas per liter of catalyst bed per hour.

The propane conversion in the PDH is from 10 to 60%, preferably from 20 to 50%, at propane selectivities of from 80 to 99.5%, frequently from 88 to 96%. The conversion of the feed gases CO, $H_2$ or other combustion gases is advantageously complete. The conversion of $H_2$ formed during the PDH is from 1 to 99%, often from 10 to 80%, frequently from 30 to 70%, depending on the propane conversion.

The reaction gas (2) from the PDH contains from about 20 to 60% by volume of $N_2$, from about 1 to 5% by volume of $CO_2$, from 0.5 to 45% by volume of $H_2O$, from about 5 to 40% by volume of propane, from about 1 to 20% by volume of propene, from about 1 to 20% by volume of $H_2$ and further byproducts, for example ethane, ethene, methane and $C_4^+$.

The reaction gas (2) from the PDH is obtained at from 400 to 650° C., more advantageously from 450 to 600° C., and from 0.3 to 10, more advantageously from 1 to 5, bar. It is cooled, countercurrently to the recycle gas (1), to temperatures which are at least 5° C., better at least 50° C., and preferably at least 100° C., above the inlet temperature of the recycle gas (1). The gas stream (3) is then further cooled in one or more stages to about 10 to 60° C., depending on the temperature on emergence from the countercurrent heat exchanger W1.

In the multistage cooling, the cooling in W2 can be effected by steam generation or by air cooling and the cooling in W3 by air, water or brine cooling, depending on the temperature level. Depending on the pressure, temperature and $H_2O$ content in the gas streams (3) to (5), water condenses and is separated from the gas stream (5) in the separator A1. Suitable gas separators are all embodiments known to a person skilled in the art and suitable for this purpose.

The cooled and if necessary partly dewatered gas stream (6) is then compressed to pressures from the pressure on emergence from the separator A1 to 50 bar. The compression can be effected either in one stage or in a plurality of stages with or without intermediate cooling. Suitable compressors V1 are all embodiments known to a person skilled in the art and suitable for this purpose, for example reciprocating and rotary compressors, screw-type compressors, diaphragm-type compressors, rotary multi-vane compressors, turbo compressors, centrifugal compressors and rotary piston blowers and centrifugal blowers; however, turbo compressors or centrifugal compressors are preferably used. Criteria for choosing the compressors are both the pressure increase and the amount of gas stream to be compressed. In the multistage compression with intermediate cooling, water and possibly further condensable components condense during the intermediate cooling and can be separated from the gas stream during or after the intermediate cooling as described above, before the gas stream is fed to the next compressor stage. The gas stream (7) compressed to the final pressure can be cooled again as described above in one or more stages, it being possible once again for water and any other condensable substances to be separated from the gas streams (7) to (9).

The compressor V1 may be operated both by means of electric motors and by means of steam or gas turbines. The choice depends on the infrastructure conditions. Frequently, driving by means of steam turbine proves most economical.

The sum of the condensed streams, for example (11)—after a pressure increase—and (12), is recirculated to the PDH, to the extent that is required for covering the $H_2O$-to-propane ratio before entry into the PDH, and the remainder is discharged and if necessary incinerated. The condensate stream (13) can be vaporized before recirculation or discharge or can be subjected to a further treatment, for example a purification, before recirculation.

The gas stream (10) is then fed to the absorption column K1, in which propane and/or propene are separated from the gas stream. Here, the gas stream (10) is brought into contact with an absorbent, which takes up the $C_3$ fraction and may take up further components. Suitable absorbents are all substances known to a person skilled in the art, the absorbents described above preferably being used. The gas stream (10) is preferably fed countercurrently to the absorbent in a plurality of stages. The absorption can be effected at from 10 to 150° C., better at from 20 to 80° C., preferably at from 30 to 60° C., and at from 1 to 50, better at from 3 to 30, preferably at from 5 to 20, bar.

Suitable absorbers K1 are all embodiments known to a person skilled in the art, as described, for example, in Thermische Trennverfahren; Klaus Sattel, VCH, 1988 (ISBN 3-527-28636-5). Columns having internals are preferable. Suitable internals are likewise all embodiments known to a person skilled in the art, for example sieve trays, dual-flow trays, bubble trays, tunnel trays, lattice trays, valve trays or irregular beds, for example comprising rings (for example from Raschig), Pall rings, Intalox saddles, Berl saddles, super saddles, toroidal saddles, Interpack packing or wire mesh rings and structured packings (for example Sulzer-Kerapak or Sulzer packing BX or CY, or, for example, packings from Montz and packings from other manufacturers). Ralu-Pak 250.YC from Raschig is particularly suitable. Internals which permit high liquid loading or irrigation density, for example unstructured beds or structured packings, are preferable. The possible irrigation density should be greater than 50, preferably greater than 80, $m^3$ of liquid per $m^2$ of free cross-sectional area per hour. The internals may be either metallic, ceramic or of plastic or may consist of a composition comprising a plurality of materials. What is important in the choice of the material for the beds and packings is that the absorbent thoroughly wets these internals.

The ratio of the streams between the absorptive (24) fed to the absorption and gas stream (10) follows the thermodynamic requirements and depends on the number of theoretical plates, the temperature, the pressure, the absorption properties of the absorbent and the required degree of separation. Ratios of from 1:1 to 50:1, in particular from 1:1 to 30:1, preferably from 1:1 to 20:1, in kg/kg, with from 1 to 40, in particular from 2 to 30, preferably from 5 to 20, theoretical plates, are usual. The definition of a theoretical plate appears in the technical literature, for example "Thermische Trennverfahren", Klaus Sattel, VCH, 1988, (ISBN 3-527-28636-5).

The gas stream (14) in which the concentration of propane and/or propene has been reduced can be fed to a quench stage in order, if required, to reduce absorbent losses. The mode of operation of a quench is explained in more detail below in the description of the desorption stage.

After leaving any quench stage, the gas stream (14) can be let down. Letting down can be effected either in one stage or in a plurality of stages by throttling without energy recovery, or in one or more stages in a gas turbine T1 with recovery of mechanical energy. In the case of the recovery of mechanical energy, it may be necessary to heat up the gas stream (14) before it is passed into the turbine. The gas stream can be heated up both directly by catalytic and noncatalytic oxidation of combustible and oxidizing components contained in the gas stream or fed in from outside, and by indirect heat supply with the aid of steam or external firing. The mechanical energy obtained during let-down can be used directly as a concomitant or main means for driving one of the compressors, preferably V1, or for generating electric power.

After the let-down, the waste gas stream (15) obtained can, depending on its purity, be fed to a catalytic or noncatalytic waste gas incineration or discharged directly into the atmosphere.

The absorbent stream (16) laden predominantly with propane (from 2 to 30% by volume) and/or propene (from 2 to 30% by volume) and possibly further components (for example $CO_2$, $C_2^-$, $C_4^+$, $H_2O$), is let down if necessary and then fed to the desorption column K2. The let-down can be effected both without recovery of the mechanical energy in one or more stages and with recovery of mechanical energy (for example in a turbine or a centrifugal pump operating in reverse). Moreover, it may be useful to heat up the stream (16) prior to desorption. This heating-up is preferably effected by means of countercurrent heat exchange with the stream (17) in W6. In addition, it may be useful to heat up stream (16) over and above this.

The desorption in K2 of propane and/or propene can be carried out by distillation, by simple flash or by stripping. The desorption is supported by reducing the pressure to 0.1 to 10, in particular to 1 to 5, preferably to 1.5 to 3, bar.

If the desorption is effected by distillation, the separation step can be carried out on the basis of all knowledge known to a person skilled in the art. A particularly simple embodiment of the desorption is the one-stage flash or flash evaporation of the laden solvent in an apparatus suitable for this purpose. It may be expedient to heat the stream (16) to 20 to 300° C., in particular to 40 to 200° C., preferably to 50 to 150° C., prior to flashing. The apparatus should be designed so that both the thermodynamic separation between propane or propene and the solvent and the fluid dynamic separation between gas and liquid take place readily. The apparatus may have, for example, a cylindrical or spherical shape, as well as other designs known to a person skilled in the art. If the apparatus is of a cylindrical shape, the cylinder may be either upright or horizontal. Viewed vertically, the feed to the flash apparatus is as a rule between the gas discharge and the liquid discharge. In the simplest case, the apparatus has no additional internals. For better thermodynamic separation, the internals such as those known to a person skilled in the art for distillation, absorption and stripping can be installed in the apparatus, in particular those described in the text above for the absorption. For better fluid dynamic separation, internals such as those known to a person skilled in the art for gas/liquid separation, for example knitted fabrics, deflector plates or the like, may additionally be integrated in the flash apparatus. Moreover, the flash apparatus may contain apparatuses which permit the introduction of heat, for example heated pipe coils or heated walls.

If, as in the present case, air or a similar stripping medium (for example steam, $N_2$, fresh propane or a further gas required in the process) is available, it is expediently used for supporting the flash process.

A special embodiment for this purpose is the multistage stripping of the volatile components propane and/or propene with the starting gas stream (25) for the oxidation (of course, as in the one-stage case, all additionally absorbed components from the stream (10) and any substances formed are also stripped according to their volatility). In the simplest case, the starting gas stream (25) is the air required for oxidizing the propene to acrolein or acrylic acid. The compression of the air or of the starting gas stream can be effected both before and after the desorption. However, the starting gas stream (25) may also contain recycled gas from the acrylic acid process and steam, fresh propane or further blanketing gaseous component in addition to the air. It is particularly advantageous if the starting gas stream (25) is fed countercurrently or crosswise to the liquid absorbent during the desorption. In the case of countercurrent flow, the desorption apparatus or desorber may be designed in the same way as the absorption column described in the text above.

The cross-flow may be expedient if the explosion range is passed through during the desorption. This is the case when the starting gas stream (25) is a lean gas mixture with respect to the combustion tendency and the gas stream (18) laden with propane and/or propene is a rich gas mixture with respect to the combustion inclination after the desorption. The gas mixture is defined as being lean in this context when the content of combustible substances is too low to be ignitable and a gas mixture is defined as rich in this context when the content of combustible substances is too high to be ignitable.

In the case of cross-flow, the total starting gas stream is not introduced into the bottom but is divided into partstreams and introduced at a plurality of suitable points along the desorption column, this being done in such a way that an ignitable gas mixture is not present at any point in the desorption apparatus. The desorption column may be arranged vertically or horizontally.

A further possibility for overcoming the explosion problem in the desorption of combustible components with $O_2$-containing gas streams, is to mix the starting gas stream, prior to entry into the desorption column, with a substance (for example propane, propene, methane, ethane, butane, $H_2O$, etc.) in such a way that the starting gas mixture is itself rich prior to entry into the desorption column. However, it is also possible to split the starting gas stream and to pass a propane- or propene-free starting gas into the bottom of the desorption column in order to achieve very good depletion of propane and/or propene in the absorptive (17) and to pass a starting gas which, for example, is enriched with propane and/or propene into that region of the desorption column in which an ignitable gas mixture can form.

After any countercurrent heat exchange (W6) and a pressure increase with the aid of a pump (P1), the absorbent stream (17) depleted in propane and/or propene can be further cooled in one or more stages (for example in W7) and fed via line (24) back to the absorber K1.

In general, the multistage desorption may take place at all pressures and temperatures.

However, pressures which are lower, and temperatures which are higher, than those in the absorption are advantageous. In the present case, pressures of from 1 to 5, in particular from 2 to 3, bar and temperatures of from 20 to 200° C., in particular from 30 to 100° C., particularly preferably from 35 to 70° C., are desirable.

The ratio of absorbent stream (17) to starting gas stream (25) follows the thermodynamic requirements and depends on the number of theoretical plates, the temperature, the pressure and the desorption properties of the absorbent and the required degree of separation. Ratios of from 1:1 to 50:1, in particular from 5:1 to 40:1, preferably from 10:1 to 30:1, in kg/kg with from 1 to 20, in particular from 2 to 15, preferably from 3 to 10, theoretical plates are usual.

In general, the starting gas stream laden with propane and/or propene can be fed without further treatment to the oxidation stages 2. However, it may be expedient to feed the starting gas stream, prior to the oxidation, to a further process stage in order, for example, to reduce the losses of concomitantly stripped absorbent. The separation of the absorbent from the laden starting gas stream for the oxidation can be carried out by all process steps known to a person skilled in the art. One possible embodiment is the quenching of the laden starting gas stream with water. In this case, the absorbent is washed out of the laden starting gas stream with water. This washing or quenching can be carried out at the top of the desorption column over a liquid collecting tray or in a separate apparatus. Internals such as those known to a person skilled in the art for distillation, absorption and desorption and as described in the text above for the absorption can be installed in the quench apparatus for supporting the separation effect. The same applies to the quench apparatus where it is designed as a separate apparatus.

After the water has washed the absorbent out of the starting gas stream laden with propane and/or propene, the water/absorbent mixture (19) can be fed to a phase separation D1, and the treated starting gas stream (18), after possible preheating, can be fed to the propene oxidation stage 2.

The phase separation can be carried out in all embodiments known to a person skilled in the art, as also used, for example, in liquid/liquid extraction. In the simplest case, these are horizontal or vertical elongated apparatuses with or without internals, in which the organic absorbent phase separates from the quench water. The diameter-to-length ratio here may be from 1:1 to 1:100, in particular from 1:1 to 1:10, preferably from 1:1 to 1:13. The apparatus may be flooded or may be operated using a gas cushion. For better isolation of the organic absorbent phase, the apparatus can be equipped with a dome from which the organic phase can be taken off. For supporting the phase separation, all internals known to a person skilled in the art for this purpose, for example knitted fabrics, wound cartridges or deflector plates, may be installed. Of course, rotating phase separators, for example centrifuges, may also be used.

After the phase separation, the absorptive (20) separated off can be recycled to the desorption. The quench water can, if required, be cooled or heated in a heat exchanger (W9) before reentering the quench apparatus. Advantageously, large amounts of water are circulated with the aid of a pump (P2). Suitable irrigation densities in the quench apparatus are greater than 30, in particular greater than 50, preferably greater than 80, but less than 1 000, in particular 500, preferably less than 300, $m^3$ of water per $m^2$ of free cross-sectional area of the quench apparatus per hour.

The water losses during quenching can be covered by condensate (21) as well as by dilute acid solution (22) from the acrylic acid preparation process. In order to avoid increasing concentrations, a part of the circulation quench water can be removed as a purge stream (23) and fed to the incineration plant or to another treatment for disposal (for example in a wastewater treatment plant).

If the gas stream (18) for the propene oxidation 2 has a temperature of <90° C., in particular <70° C. at pressures of from 1 to 3 bar, it may be expedient also to add water to this stream. This can be effected by admixing steam or by saturating the stream (18) in a water saturator in a manner known to a person skilled in the art. The gas stream treated in this manner has a composition of from 30 to 70% by volume of $N_2$, from 5 to 20% by volume of $O_2$, from 2 to 15% by volume of propene, from 2 to 40% by volume of propane and from 0.5 to 25% by volume of $H_2O$ and contains further components, for example $CO_2$, methane, ethane, ethene and $C_4^+$. It can be fed to the oxidation 2, which can be carried out as described above or as disclosed in the patent literature. The propene or acrolein oxidation can be carried out in salt bath reactors, for example from Deggendorfer-Werft according to the prior art or in other reactor types. An air feed or steam feed may or may not once again take place between the first oxidation stage to acrolein and the second oxidation stage to acrylic acid. The higher $C_3$ content in the gas (18) with the oxidation 2 in any case requires removal of the heat of reaction from the reaction space. Propene loadings of from 5 to 350, in particular from 90 to 300, preferably from 100 to 250, l(S.T.P.) of propene per liter of catalyst bed per hour are suitable.

The separation of the acrylic acid from the reaction gas (26) of the oxidation 2 in stage 3 can be carried out as described above using, for example, a high-boiling solvent, such as a mixture of diphyl and dimethyl phthalate, or by absorption in water and by fractional condensation.

The purification of the acrylic acid can be effected by stripping and distillation or by azeotropic distillation or by crystallization.

The process described in FIG. 7 is suitable both for retrofitting of all existing plants for the production of acrolein and/or acrylic acid and in combination with new acrylic acid plants.

Surprisingly, it was found that, in spite of the usually expected residues of absorbent in the gas B, no problems occurred with the oxidation or with the oxidation catalyst. Moreover, no problems were observed with any oxidation products which may form from the absorbent during the oxidation. Where problems occur with residues of absorbent, which as a rule is not the case when hydrocarbons having a high boiling point, in particular paraffins, are used as absorbent, said absorbent can be removed, for example by a water quench or by adsorption.

It was therefore surprising that absorption can be used in the novel process. In contrast to the adsorption used in the Japanese publication JP-A-10 36311, the absorption used here for propane and/or propene is substantially easier and more economical to handle.

Furthermore, the present invention has the advantage that existing plants for the preparation of acrolein and/or acrylic acid which use propene as a starting material can be converted in an advantageous manner to the more economical propane as a starting material.

The example which follows and which describes the preferred embodiment of the novel process illustrates the invention.

EXAMPLE

Acrylic acid is prepared by a process as shown in FIG. 7. The reference numerals used below therefore relate to FIG. 7.

2090 l(S.T.P.)/h of the recycle gas (1) from the working-up stage 3, which is obtained at a temperature of 30° C. and a pressure of 1.2 bar, are compressed to 2.0 bar with the aid of a compressor V0 and heated to 450° C. in a heat exchanger W1 countercurrently to the reaction gas (2) from the propane dehydrogenation (PDH). The stated pressure in bar relates here and below in this example to the absolute pressure.

The recycle gas stream (1) contains 60.3% by volume of $N_2$, 1.2% by volume of $CO_2$, 0.5% by volume of CO, 3.4% by volume of $O_2$, 1.9% by volume of $H_2O$, 32.2% by volume of propane and 0.4% by volume of propene and further oxidation byproducts. Before the heating-up, 170 l(S.T.P.)/h of fresh propane (3) and steam (4) are mixed with the recycle gas stream before it is passed into the PDH. The fresh propane used is industrial propane (>98% propane content with 100 ppm by weight of $C_4^+$ fraction). The molar ratio of steam to propane in the gas stream is 0.5.

The gas mixture is fed to the 1st reactor of 4 reactors. The internal diameter of the reactors is 50 mm. The reactors are designed in such a way that they can be operated autothermally. Each reactor contains a 110 mm high catalyst bed comprising extrudates (d=3 mm, l=5 mm).

In the 4 reactors, propane undergoes 20% conversion at a propene selectivity of 92%.

The reaction gas (2) from the PDH contains 44.9% by volume of $N_2$, 2.7% by volume of $CO_2$, 16.9% by volume of $H_2O$, 24.0% by volume of propane, 5.8% by volume of propene, 5.5% by volume of $H_2$ and small amounts of further byproducts, for example ethane, ethene, methane and $C_4^+$.

The reaction gas (2) from the PDH is obtained at 520° C. and 1.5 bar and is cooled to 30° C. On average, about 350 g of water (11) per hour condense.

The cooled gas stream (6) is then compressed in one stage in a piston compressor to 7.5 bar and is cooled again to 30° C. The condensed water (12) is combined with the condensation (11) and is partly vaporized and mixed with the recycle gas stream (1). A further part (stream (21)) is fed to the quench. The remainder is discharged.

2 340 l(S.T.P.)/h of the gas stream (10) are then passed into the bottom of the absorption column K1 (metal wall, internal diameter=80 mm, column length 3 m). 60% of the volume of the absorption column are filled with packing elements from Montz (Montz-Pak type B1).

The gas stream (10) contains 53.9% by volume of nitrogen, 3.3% by volume of carbon dioxide, 0.4% by volume of water, 28.8% by volume of propane, 7.0% by volume of propene, 6.6% by volume of hydrogen and small amounts of further byproducts, for example ethane, ethene, methane and $C_{4+}$.

35 kg/h of low-$C_3$ tetradecane (24) from the desorption column are passed at 30° C. to the top of the absorption column K1.

The waste gas stream (14) still contains 1150 ppm by volume of propane and 750 ppm by volume of propene. The waste gas stream (14) from the absorption column is let down to ambient temperature and ambient pressure, respectively, via a pressure control valve and then incinerated.

The laden absorbent stream (16) is removed from the bottom of the column K1, let down to 2.4 bar via a pressure control valve and fed to the top of the desorption column K2.

The desorption column K2 has the same dimensions as the absorption column K1 and is loaded in the same manner with packings.

1310 l(S.T.P.) of compressed air at 2.45 bar and 30° C. are passed into the bottom of the desorption column. The desorption column is thermostated at 40° C.

The exit gas from the desorption column (2190 l(S.T.P.)/h) contains 30.7% by volume of propane, 7.4% by volume of propene, 12.3% by volume of $O_2$, 46.4% by volume of $N_2$, 1.5% by volume of $H_2O$ and 1.6% by volume of $CO_2$ and small residues of tetradecane and is passed into a quench apparatus, which is located in the top of the desorption column K2.

The bottom discharge of the desorption column K2 is transported via the pump P1 and the heat exchanger W7 to the top of the absorption column K1.

The quench apparatus is a metal column likewise having an internal diameter of 80 mm and is equipped with internals of the same type as those in the absorption column K1. The water quench is operated at 30° C. In the quench apparatus, about 120 l of water per hour are sprayed onto the bed. A two-phase liquid mixture is removed from the bottom of the quench apparatus and is passed into a phase separator. The phase separator is a horizontal container having a diameter of 200 mm and a length of 500 mm and contains a fine knitted wire fabric which is installed in the first third of the phase separator, in the direction of flow. The aqueous phase removed from the phase separator D1 is pumped back to the top of the quench apparatus. On average, about 1 g of tetradecane per hour is removed from the phase separator and passed into the tetradecane storage vessel. The water losses during quenching are compensated by condensation water (21).

The exit gas stream from the water quench is heated to 200° C. before it is fed to the two-stage oxidation.

The oxidation takes place in model tubes having an internal diameter of 26 mm and a length of 4 m. The first model tube is filled with 2.7 m of a catalyst as described in EP-A-0 575 879 and the second model tube is filled with 3 m of a catalyst as described in EP-A-0 017 000. 315 l(S.T.P.) of fresh air are additionally passed per hour between the first and second oxidation stage.

The isolation of the acrylic acid from the reaction gas (26) of the oxidation and the purification of said acrylic acid are effected as described in EP-A-0 982 289.

According to this process, on average 440 g of crude acrylic acid (27) comprising >99.5% of acrylic acid are obtained per hour.

We claim:

1. A process for the preparation of at least one of acrolein and acrylic acid from at least one of propane and propene, the process comprising the following steps:
   (a) separating at least one of propane and propene from a gas mixture A containing at least one of propane and propene by absorption in an absorbent,
   (b) separating at least one of propane and propene from the absorbent to give a gas B containing at least one of propane and propene and
   (c) oxidizing the gas B obtained in stage (b) to form at least one of acrolein and acrylic acid,
   wherein no heterogeneously catalyzed dehydrogenation of propane without a supply of oxygen is carried out between steps (b) and (c), and
   wherein the separating in step (b) is carried out by stripping with at least one of a pressure change and a temperature change, using at least one of steam, air and an oxygen/nitrogen mixture, and
   wherein during the separating (a) the gas mixture A is brought into contact with the absorbent at a pressure of from 1 to 50 bar, and
   wherein the stripping (b) is carried out at a pressure of from 0.1 to 10 bar.

2. The process as claimed in claim 1, wherein the gas mixture A further comprises at least one component selected from the group consisting of hydrogen, nitrogen and oxides of carbon.

3. The process as claimed in claim 1, wherein at least one $C_8$-$C_{20}$-alkane or $C_8$-$C_{20}$-alkene is used as the absorbent in step (a).

4. The process as claimed in claim 1, wherein, in step (c), propene is oxidized to at least one of acrolein and acrylic acid.

5. The process as claimed in claim 1, wherein, in step (c), propane is oxidized to at least one of acrolein and acrylic acid.

6. The process as claimed in claim 5, wherein a multimetal oxide material of the formula (I)

$$MoV_bM^1_cM^2_dO_n \qquad (I)$$

where
$M^1$ is at least one of Te or Sb,
$M^2$ is at least one element selected from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In,
b is from .0.01 to 1,
c is from >0 to 1,
d is from >0 to 1, and
n is a number which is determined by the valency and frequency of the elements other than oxygen in (I),
is used as the catalyst for oxidizing propane in step (c).

7. The process as claimed in claim 1, wherein the gas mixture A used in step (a) has the composition of a gas mixture which is obtained by at least one of homogeneous or heterogeneously catalyzed dehydrogenation of propane to propane.

8. The process as claimed in claim 7, wherein the propane dehydrogenation is carried out with a supply of oxygen.

9. The process as claimed in claim 1, wherein, after step (c) has been carried out, unconverted propane and optionally propene is subjected to a propane dehydrogenation and the product mixture obtained is subjected to step (a) again.

10. The process as claimed in claim 1, wherein step (c) is carried out directly after step (b).

11. The process as claimed in claim 1, wherein after step (b) and before step (c) a water quench is carried out for separating absorbent.

12. A process for the preparation of at least one of acrolein and acrylic acid from at least one of propane and propene, the process comprising the following steps:
   (a) separating at least one of propane and propene from a gas mixture A containing at least one of propane and propene by absorption in an absorbent,
   (b) separating at least one of propane and propene from the absorbent to give a gas B containing at least one of propane and propene and
   (c) oxidizing the gas B obtained in stage (b) to form at least one of acrolein and acrylic acid,
   wherein no heterogeneously catalyzed dehydrogenation of propane without a supply of oxygen is carried out between steps (b) and (c),
   wherein, after step (c) has been carried out, at least one of unconverted propane and unconverted propene is separated off according to steps (a) and (b) and is recycled to step (c), and
   wherein the separating in step (b) is carried out by stripping with at least one of a pressure change and a temperature change, using at least one of steam, air and an oxygen/nitrogen mixture, and
   wherein during the separating (a) the gas mixture Ais brought into contact with the absorbent at a pressure of from 1 to 50 bar, and
   wherein the stripping (b) is carried out at a pressure of from 0.1 to 10 bar.

13. The process as claimed in claim 12, wherein, in step (c), propene is oxidized to at least one of acrolein and acrylic acid.

14. The process as claimed in claim 12, wherein, in step (c), propane is oxidized to at least one of acrolein and acrylic acid.

15. The process as claimed in claim 12, wherein the gas mixture A used in step (a) has the composition of a gas mixture which is obtained by at least one of homogeneous or heterogeneously catalyzed dehydrogenation of propane to propene.

16. The process as claimed in claim 12, wherein, after step (c) has been carried out, unconverted propane and optionally propene is subjected to a propane dehydrogenation and the product mixture obtained is subjected to step (a) again.

17. The process as claimed in claim 12, wherein step (c) is carried out directly after step (b).

18. The process as claimed in claim 12, wherein after step (b) and before step (c) a water quench is carried out for separating absorbent.

19. The process as claimed in claim 1, further comprising:
dehydrogenating propane by heterogeneous catalysis in the presence of oxygen.

20. The process as claimed in claim 12, further comprising:
dehydrogenating propane by heterogeneous catalysis in the presence of oxygen.

21. The process as claimed in claim 1, wherein the oxidizing is carried out in the presence of an oxidation catalyst with substantially no decrease in the activity of the oxidation catalyst.

22. The process as claimed in claim 1, wherein the absorbent is an organic solvent having a boiling point of from 200 to 350° C.

23. The process as claimed in claim 1, wherein the absorbent is tetradecane.

24. The process as claimed in claim 1, further comprising: quenching gas B after the separating (b).

25. The process as claimed in claim 24, wherein quenching includes spraying water into the gas B to form a two phase mixture and separating an aqueous phase of the two phase mixture from an organic phase of the two phase mixture.

26. The process as claimed in claim 25, wherein the organic phase of the two phase liquid comprises the absorbent.

27. The process as claimed in claim 12, wherein the oxidizing is carried out in the presence of an oxidation catalyst with substantially no decrease in the activity of the oxidation catalyst.

28. The process as claimed in claim 12, wherein the absorbent is an organic solvent having a boiling point of from 200 to 350° C.

29. The process as claimed in claim 12, wherein the absorbent is tetradecane.

30. The process as claimed in claim 12, further comprising:
quenching gas B after the separating (b).

31. The process as claimed in claim 30, wherein the quenching includes spraying water into the gas B to form a two phase mixture and separating an aqueous phase of the two phase mixture from an organic phase of the two phase mixture.

32. The process as claimed in claim 31, wherein the organic phase of the two phase liquid comprises the absorbent.

33. The processes claimed in claim 1, wherein any hydrogen present in the gas mixture A is not present after the separating (b).

34. The processes claimed in claim 12, wherein any hydrogen present in the gas mixture A is not present after the separating (b).

35. The process as claimed in claim 1, wherein the stripping is carried out using air.

36. The process as claimed in claim 12, wherein the stripping is carried out using air.

37. The process as claimed in claim 1, wherein the stripping (b) is carried out at a pressure of from 1 to 5 bar, and the gas mixture A is contacted with the absorbent at a temperature of from 30 to 50° C.

38. The process as claimed in claim 12, wherein the stripping (b) is carried out at a pressure of from 1 to 5 bar, and the gas mixture A is contacted with the absorbent at a temperature of from 30 to 50° C.

\* \* \* \* \*

UNITED STATES PATENT AND TRADEMARK OFFICE
CERTIFICATE OF CORRECTION

PATENT NO. : 7,321,058 B2  
APPLICATION NO. : 10/297579  
DATED : January 22, 2008  
INVENTOR(S) : Otto Machhammer et al.

Page 1 of 1

It is certified that error appears in the above-identified patent and that said Letters Patent is hereby corrected as shown below:

On the title page, Item (30), the Foreign Application Priority Data is incorrect. Item (30) should read as follows:

-- (30) Foreign Application Priority Data

Jun. 14, 2000 (DE).......................10028582  
Jun. 20, 2000 (DE).......................10029338  
July 7, 2000 (DE).......................10033121  
July 18, 2000 (DE).......................10034825  
Sept. 20, 2000 (DE).......................10046672  
Oct. 17, 2000 (DE).......................10051419  
April 17, 2001 (DE).......................10118814  
April 23, 2001 (DE).......................10119933  
May 3, 2001 (DE).......................10121592  
May 7, 2001 (DE).......................10122027 --

Signed and Sealed this

Twentieth Day of May, 2008

JON W. DUDAS  
*Director of the United States Patent and Trademark Office*